United States Patent [19]

Hong et al.

[11] Patent Number: 5,728,651
[45] Date of Patent: Mar. 17, 1998

[54] HERBICIDAL TRIAZOLINONES

[75] Inventors: Wonpyo Hong, Hockessin, Del.; Karlheinz Drauz, Freigericht; Matthias Schafer, Haibach, both of Germany; William Thomas Zimmerman, Landenberg, Pa.

[73] Assignees: E. I. du Pont de Nemours and Company, Wilmington, Del.; Degussa Aktiengesellschaft, Frankfurt, Germany

[21] Appl. No.: 525,616

[22] PCT Filed: Mar. 8, 1994

[86] PCT No.: PCT/US94/02498

§ 371 Date: Sep. 26, 1995

§ 102(e) Date: Sep. 26, 1995

[87] PCT Pub. No.: WO94/22860

PCT Pub. Date: Oct. 13, 1994

Related U.S. Application Data

[63] Continuation-in-part of Ser. No. 38,730, Mar. 26, 1993, abandoned.

[51] Int. Cl.⁶ .......................... A01N 43/90; C07D 471/04
[52] U.S. Cl. .............................................. 504/246; 546/119
[58] Field of Search .................... 504/246; 546/119

[56] References Cited

U.S. PATENT DOCUMENTS 4,213,773  7/1980  Wolf .............................................. 71/92

FOREIGN PATENT DOCUMENTS 311135  4/1989  European Pat. Off. .

*Primary Examiner*—Patricia L. Morris

[57] ABSTRACT

Compounds of Formula I having herbicidal utility are disclosed

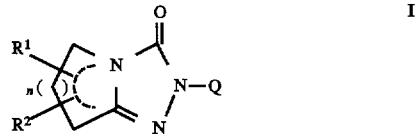

wherein the left-hand ring contains only single bonds or one bond in the ring is a double bond, and $R^1$, $R^2$, Q and n are defined in the text, including compositions containing such compounds and a method for controlling weeds employing such compounds.

10 Claims, No Drawings

HERBICIDAL TRIAZOLINONES

CROSS-REFERENCE TO RELATED APPLICATIONS

This application is the international application of PCT/US94/02498 filed under 35 U.S.C. 371, which is a continuation-in-part of U.S. Ser. No. 08/038,730 filed Mar. 26, 1993 now abandoned.

BACKGROUND OF THE INVENTION

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around railroad tracks, storage tanks and industrial storage areas. There are many products commercially available for these purposes, but the search continues for products which are more effective, less costly and environmentally safe.

U.S. Pat. No. 4,213,773 discloses herbicidal triazolinones which differ from the compounds of the present invention in that they lack a substituent on the left-hand ring.

SUMMARY OF THE INVENTION

The crop protection chemical compounds of this invention are compounds of Formula I:

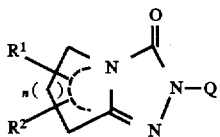

wherein the dashed line indicates that the left-hand ring contains only single bonds or one bond in the ring is a double bond;

n is 1 or 2;

$R^1$ is selected from the group H, halogen; hydroxy, $C_1-C_3$ alkoxy; $C_1-C_3$ haloalkoxy; $C_2-C_5$ alkylcarbonyloxy; or $C_2-C_5$ haloalkylcarbonyloxy;

$R^2$ is selected from the group H, hydroxy, and halogen; or when $R^1$ and $R^2$ are bonded to the same carbon atom they can be taken together along with the carbon to which they are attached to form C=O; or when $R^1$ and $R^2$ are bonded to adjacent carbon atoms they can be taken together along with the carbons to which they are attached to form

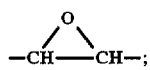

Q is selected from the group

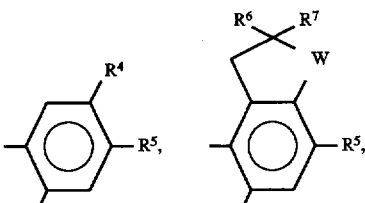

Q-1    Q-2

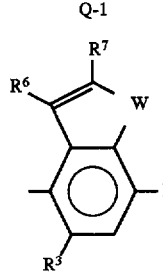    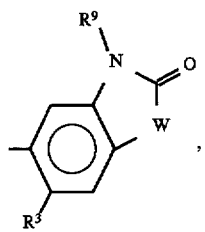

Q-3    Q-4

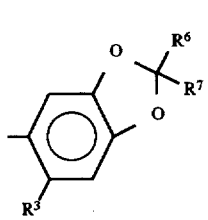    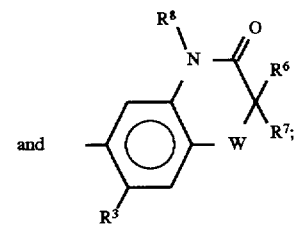

and

Q-5    Q-6

$R^3$ is selected from the group H and halogen;

$R^4$ is selected from the group H, $C_1-C_8$ alkyl, $C_1-C_8$ haloalkyl, halogen, $OR^9$, $S(O)_mR^9$, $COR^9$, $CO_2R^9$, $C(O)SR^9$, $C(O)NR^{11}R^{12}$, CHO, $CR^7=CR^7CO_2R^9$, $CO_2N=CR^{13}R^{14}$, $NO_2$, CN, $NHSO_2R^{15}$ and $NHSO_2NHR^{15}$;

m is 0, 1 or 2;

$R^5$ is selected from the group $C_1-C_2$ alkyl, $C_1-C_2$ haloalkyl, $OCH_3$, $SCH_3$, $OCHF_2$, halogen, CN and $NO_2$;

$R^6$ is selected from the group H, $C_1-C_3$ alkyl, $C_2-C_3$ alkynyl, $C_2-C_3$ haloalkynyl, $CO_2(C_1-C_4$ alkyl), and halogen;

$R^7$ is independently selected from the group H, $C_1-C_3$ alkyl and halogen; or when Q is Q-2 or Q-6, $R^6$ and $R^7$ together with the carbon to which they are attached can be C=O;

$R^8$ is selected from the group $C_1-C_6$ alkyl, $C_1-C_6$ haloalkyl, $C_2-C_6$ alkoxyalkyl, $C_3-C_6$ alkenyl and $C_3-C_6$ alkynyl;

$R^9$ is selected from the group $C_1-C_8$ alkyl; $C_3-C_8$ cycloalkyl; $C_3-C_8$ alkenyl; $C_3-C_8$ alkynyl; $C_1-C_8$ haloalkyl; $C_2-C_8$ alkoxyalkyl; $C_2-C_8$ alkylthioalkyl; $C_2-C_8$ alkylsulfinylalkyl; $C_2-C_8$ alkylsulfonylalkyl; $C_1-C_8$ alkylsulfonyl; phenylsulfonyl optionally substituted on the phenyl ring with halogen or $C_1-C_4$ alkyl; $C_4-C_8$ alkoxyalkoxyalkyl, $C_4-C_8$ cycloalkylalkyl; $C_4-C_8$ alkenoxyalkyl; $C_4-C_8$ alkynoxyalkyl; $C_6-C_8$ cycloalkoxyalkyl; $C_4-C_8$ alkenyloxyalkyl; $C_4-C_8$ alkynyloxyalkyl; $C_3-C_8$ haloalkoxyalkyl; $C_4-C_8$ haloalkenoxyalkyl; $C_4-C_8$ haloalkynoxyalkyl; $C_6-C_8$ cycloalkylthioalkyl; $C_4$–$C_8$ alkenylthioalkyl; $C_4$–$C_8$ alkynylthioalkyl; $C_1$–$C_4$ alkyl substituted a substituent selected from phenoxy and benzyloxy, each ring optionally substituted with a substituent selected from halogen, $C_1$–$C_3$ alkyl and $C_1$–$C_3$ haloalkyl; $C_4$–$C_8$ trialkylsilylalkyl; $C_3$–$C_8$ cyanoalkyl; $C_3$–$C_8$ halocycloalkyl; $C_3$–$C_8$ haloalkenyl; $C_5$–$C_8$ alkoxyalkenyl; $C_5$–$C_8$ haloalkoxyalkenyl; $C_5$–$C_8$ alkylthioalkenyl; $C_3$–$C_8$ haloalkynyl; $C_5$–$C_8$ alkoxyalkynyl; $C_5$–$C_8$ haloalkoxyalkynyl; $C_5$–$C_8$ alkylthioalkynyl; $C_2$–$C_8$ alkyl carbonyl; benzyl optionally substituted with a substituent selected from the group halogen, $C_1$–$C_3$ alkyl and $C_1$–$C_3$ haloalkyl; $CHR^{16}COR^{10}$; $CHR^{16}CO_2R^{10}$; $CHR^{16}P(O)(OR^{10})_2$; $CHR^{16}P(S)(OR^{10})_2$; $CHR^{16}C(O)NR^{11}R^{12}$; and $CHR^{16}C(O)NH_2$;

$R^{10}$ is selected from the group $C_1$–$C_6$ alkyl, $C_1$–$C_6$ alkenyl and $C_1$–$C_6$ alkynyl;

$R^{11}$ and $R^{13}$ are independently selected from the group H and $C_1$–$C_4$ alkyl;

$R^{12}$ and $R^{14}$ are independently selected from the group $C_1$–$C_4$ alkyl and phenyl optionally substituted with a substituent selected from the group halogen, $C_1$–$C_3$ alkyl and $C_1$–$C_3$ haloalkyl;

$R^{11}$ and $R^{12}$ may be taken together as —$(CH_2)_5$—, —$(CH_2)_4$— or —$CH_2CH_2OCH_2CH_2$—, each ring optionally substituted with a substituent selected from the group $C_1$–$C_3$ alkyl, phenyl and benzyl;

$R^{13}$ and $R^{14}$ may be taken together with the carbon to which they are attached to form $C_3$–$C_8$ cycloalkyl;

$R^{15}$ is selected from the group $C_1$–$C_4$ alkyl and $C_1$–$C_4$ haloalkyl;

$R^{16}$ is selected from the group H and $C_1$–$C_3$ alkyl; and

W is selected from the group O and S;

provided that $R^1$ is other than H when the left-hand ring contains only single bonds.

In the above definitions, the terms "alkyl", "alkenyl" and "alkynyl" include straight and branched chain groups. "Halogen" means fluorine, chlorine, bromine or iodine. Further, when used in compound words such as "haloalkyl" said alkyl may be partially or fully saturated with halogen atoms, which may be the same or different.

The bonding in compounds of Formula I is such that the left-hand ring contains single bonds, except that at most one of the bonds may be a double bond. Examples of structures of Formula I are:

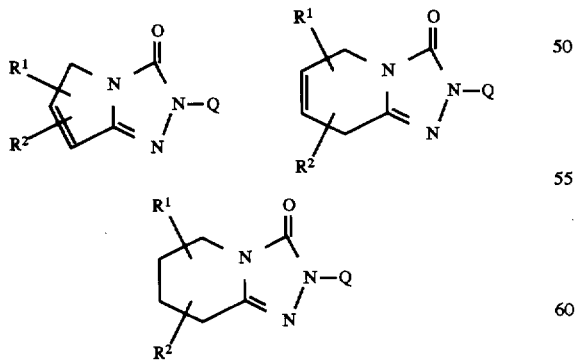

Preferred for reasons of better biological activity and/or ease of synthesis are: Preferred 1: Compounds of Formula I wherein the left-hand ring contains only single bonds. Such compounds are compounds of Formula Ia:

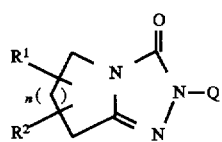

wherein n is 1 or 2;

$R^1$ is selected from the group halogen; hydroxy, $C_1$–$C_3$ alkoxy; $C_1$–$C_3$ haloalkoxy; $C_2$–$C_5$ alkylcarbonyloxy; or $C_2$–$C_5$ haloalkylcarbonyloxy;

$R^2$ is selected from the group H, hydroxy, and halogen; or when $R^1$ and $R^2$ are bonded to the same carbon atom they can be taken together along with the carbon to which they are attached to form C=O; or when $R^1$ and $R^2$ are bonded to adjacent carbon atoms they can be taken together along with the carbons to which they are attached to form

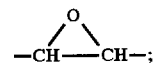

Q is selected from the group

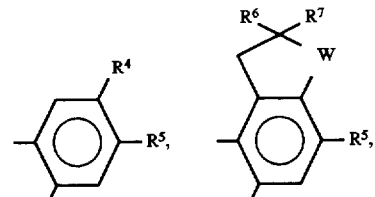

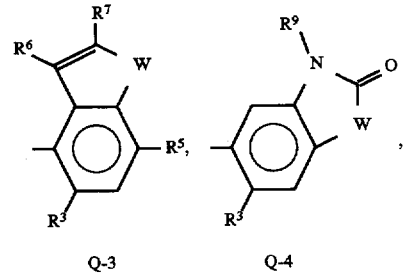

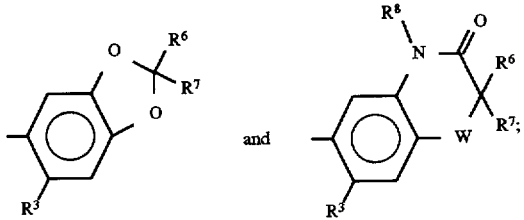

$R^3$ is selected from the group H and halogen;

$R^4$ is selected from the group H, $C_1$–$C_8$ alkyl, $C_1$–$C_8$ haloalkyl, halogen, $OR^9$, $S(O)_mR^9$, $COR^9$, $CO_2R^9$, $C(O)SR^9$, $C(O)NR^{11}R^{12}$, CHO, $CR^7$=$CR^7CO_2R^9$, $CO_2N$=$CR^{13}R^{14}$, $NO_2$, CN, $NHSO_2R^{15}$ and $NHSO_2NHR^{15}$;

m is 0, 1 or 2;

$R^5$ is selected from the group $C_1$–$C_2$ alkyl, $C_1$–$C_2$ haloalkyl, $OCH_3$, $SCH_3$, $OCHF_2$, halogen, CN and $NO_2$;

$R^6$ is selected from the group H, $C_1$–$C_3$ alkyl, $C_2$–$C_3$ alkynyl, $C_2$–$C_3$ haloalkynyl, $CO_2(C_1$–$C_4$ alkyl), and halogen;

$R^7$ is independently selected from the group H, $C_1$–$C_3$ alkyl and halogen; or when Q is Q-2 or Q-6, $R^6$ and $R^7$ together with the carbon to which they are attached can be C=O;

$R^8$ is selected from the group $C_1$–$C_6$ alkyl, $C_1$–$C_6$ haloalkyl, $C_2$–$C_6$ alkoxyalkyl, $C_3$–$C_6$ alkenyl and $C_3$–$C_6$ alkynyl;

$R^9$ is selected from the group $C_1$–$C_8$ alkyl; $C_3$–$C_8$ cycloalkyl; $C_3$–$C_8$ alkenyl; $C_3$–$C_8$ alkynyl; $C_1$–$C_8$ haloalkyl; $C_2$–$C_8$ alkoxyalkyl; $C_2$–$C_8$ alkylthioalkyl; $C_2$–$C_8$ alkylsulfinylalkyl; $C_2$–$C_8$ alkylsulfonylalkyl; $C_1$–$C_8$ alkylsulfonyl; phenylsulfonyl optionally substituted on the phenyl ring with halogen or $C_1$–$C_4$ alkyl; $C_4$–$C_8$ alkoxyalkoxyalkyl, $C_4$–$C_8$ cycloalkylalkyl; $C_4$–$C_8$ alkenoxyalkyl; $C_4$–$C_8$ alkynoxyalkyl; $C_6$–$C_8$ cycloalkoxyalkyl; $C_4$–$C_8$ alkenyloxyalkyl; $C_4$–$C_8$ alkynyloxyalkyl; $C_3$–$C_8$ haloalkoxyalkyl; $C_4$–$C_8$ haloalkenoxyalkyl; $C_4$–$C_8$ haloalkynoxyalkyl; $C_6$–$C_8$ cycloalkylthioalkyl; $C_4$–$C_8$ alkenylthioalkyl; $C_4$–$C_8$ alkynylthioalkyl; $C_1$–$C_4$ alkyl substituted a substituent selected from phenoxy and benzyloxy, each ring optionally substituted with a substituent selected from halogen, $C_1$–$C_3$ alkyl and $C_1$–$C_3$ haloalkyl; $C_4$–$C_8$ trialkylsilylalkyl; $C_3$–$C_8$ cyanoalkyl; $C_3$–$C_8$ halocycloalkyl; $C_3$–$C_8$ haloalkenyl; $C_5$–$C_8$ alkoxyalkenyl; $C_5$–$C_8$ haloalkoxyalkenyl; $C_5$–$C_8$ alkylthioalkenyl; $C_3$–$C_8$ haloalkynyl; $C_5$–$C_8$ alkoxyalkynyl; $C_5$–$C_8$ haloalkoxyalkynyl; $C_5$–$C_8$ alkylthioalkynyl; $C_2$–$C_8$ alkyl carbonyl; benzyl optionally substituted with a substituent selected from the group halogen, $C_1$–$C_3$ alkyl and $C_1$–$C_3$ haloalkyl; $CHR^{16}COR^{10}$; $CHR^{16}CO_2R^{10}$; $CHR^{16}P(O)(OR^{10})_2$; $CHR^{16}P(S)(OR^{10})_2$; $CHR^{16}C(O)NR^{11}R^{12}$; and $CHR^{16}C(O)NH_2$;

$R^{10}$ is selected from the group $C_1$–$C_6$ alkyl, $C_1$–$C_6$ alkenyl and $C_1$–$C_6$ alkynyl;

$R^{11}$ and $R^{13}$ are independently selected from the group H and $C_1$–$C_4$ alkyl;

$R^{12}$ and $R^{14}$ are independently selected from the group $C_1$–$C_4$ alkyl and phenyl optionally substituted with a substituent selected from the group halogen, $C_1$–$C_3$ alkyl and $C_1$–$C_3$ haloalkyl;

$R^{11}$ and $R^{12}$ may be taken together as —$(CH_2)_5$—, —$(CH_2)_4$— or —$CH_2CH_2OCH_2CH_2$—, each ring optionally substituted with a substituent selected from the group $C_1$–$C_3$ alkyl, phenyl and benzyl;

$R^{13}$ and $R^{14}$ may be taken together with the carbon to which they are attached to form $C_3$–$C_8$ cycloalkyl;

$R^{15}$ is selected from the group $C_1$–$C_4$ alkyl and $C_1$–$C_4$ haloalkyl;

$R^{16}$ is selected from the group H and $C_1$–$C_3$ alkyl; and

W is selected from the group O and S.

Preferred 2: Compounds of Formula I wherein:

$R^1$ is halogen;

$R^2$ is selected from the group H, and halogen;

Q is selected from the group consisting of Q-1, Q-2 and Q-6;

$R^3$ is halogen;

$R^5$ is selected from the group $C_1$–$C_2$ haloalkyl, $OCH_3$, $OCHF_2$, CN, $NO_2$, and halogen;

$R^6$ is selected from the group H, $C_1$–$C_3$ alkyl, $C_2$–$C_3$ alkynyl, $C_2$–$C_3$ haloalkynyl, and halogen;

$R^7$ is H; and

W is O.

Preferred 3: Compounds of Preferred 2 wherein:

$R^4$ is selected from the group halogen, $OR^9$, $S(O)_mR^9$, $COR^9$, $CO_2R^9$, $C(O)NR^{11}R^{12}$, $CH=CHCO_2R^9$, $NHSO_2R^{15}$ and $NHSO_2NHR^{15}$;

$R^5$ is halogen;

$R^6$ is selected from the group H and $C_1$–$C_3$ alkyl;

$R^7$ is H; and $R^9$ is selected from the group $C_1$–$C_8$ alkyl; $C_3$–$C_8$ cycloalkyl; $C_3$–$C_8$ alkenyl; $C_3$–$C_8$ alkynyl; $C_1$–$C_8$ haloalkyl; $C_2$–$C_8$ alkoxyalkyl; $C_1$–$C_4$ alkyl substituted with a substituent selected from phenoxy and benzyloxy, each ring optionally substituted with a substituent selected from halogen, $C_1$–$C_3$ alkyl and $C_1$–$C_3$ haloalkyl; $C_3$–$C_8$ haloalkenyl; $C_3$–$C_8$ haloalkynyl; $C_2$–$C_8$ alkyl carbonyl; benzyl optionally substituted with a substituent selected from the group halogen, $C_1$–$C_3$ alkyl and $C_1$–$C_3$ haloalkyl; $CHR^{16}COR^{10}$; $CHR^{16}CO_2R^{10}$; $CHR^{16}P(O)(OR^{10})_2$; $CHR^{16}C(O)NR^{11}R^{12}$; and $CHR^{16}C(O)NH_2$.

Preferred compounds of the invention are:

2,5,6,7-tetrahydro-2-[2,4-dichloro-5-(2-propynyloxy)phenyl]-6-fluoro-3H-pyrrolo[2,1-c]-1,2,4-triazol-3-one; and 5,6,7,8-tetrahydro-2-[2,4-dichloro-5-(2-propynyloxy)phenyl]-8-chloro-1,2,4-triazolo[4,3-α]pyridin-3(2H)-one.

Compounds of General Formula I can be readily prepared by one skilled in the art by using the reactions and techniques described in Schemes 1 to 11 below. The substituents $R^1$–$R^{16}$, n, m, and Q for the compounds illustrated are as defined as for compounds of Formula I. Compounds prepared by Schemes 1 to 11 that include compounds numbered II to XVI are intermediates or reagents for the ultimate preparation of compounds of Formula I. Compounds of Formulae Ia–It are subsets of compounds of Formula I. In cases where the substituent of a starting material is not compatible with the reaction conditions described for any of the reaction schemes, it can be assumed that the substituent is convened to a protected form prior to the described reaction scheme and then deprotected after the reaction using commonly accepted protecting/deprotecting techniques (as an example, see T. W. Greene and P. G. M. Wuts, "Protective Groups in Organic Synthesis", 2nd Edition, John Wiley and Sons, Inc., New York, 1991). Otherwise alternative approaches known to one skilled in the art are available.

One skilled in the art will recognize that compounds of Formula I may exist as multiple stereoisomers. This invention therefore, comprises racemic mixtures, enriched mixtures, and pure enantiomers of compounds of Formula I.

The compounds of this invention are made by the following processes.

A retrosynthetic analysis of compounds of Formula Ib (compounds of Formula I wherein n is 2) is shown below (Scheme 1). The formation of ring A can be accomplished by an intramolecular cyclization between the nitrogen in ring B and the terminal double bond of triazolinone of Formula II.

Scheme 1

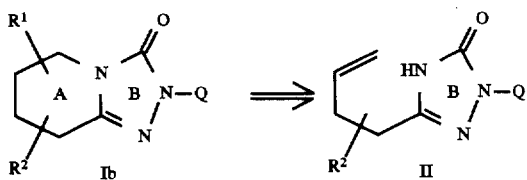

The synthesis of the triazolinone ring B in compounds of Formula II is known in the art and can be prepared by methods such as those described in U.S. Pat. No. 4,818,275 and U.S. Pat. No. 4,818,276. Acidic condensation of α-ketoacids of Formula III and phenyl hydrazine derivatives of Formula IV gives hydrazones of Formula V. Schmidt rearrangement of the acid of Formula V with diphenylphosphoryl azide followed by a ring cyclization gives triazolinones of Formula II as shown below (Scheme 2).

Scheme 2

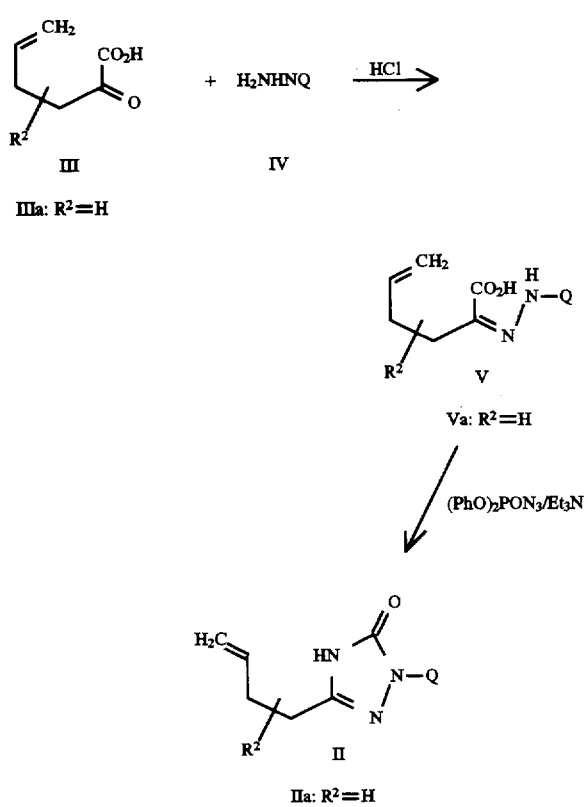

For the synthesis of the triazolinones of Formula IIa (compounds of Formula II wherein $R^2$ is H), 2-oxo-5-hexanoic acid IIIa (compound of Formula III wherein $R^2$ is H) can be used as the starting material (Scheme 3). 2-Oxo-5-hexanoic acid can be made by hydrolysis of the methyl ester of Formula VI with base, preferably one equivalent of potassium hydroxide in an aqueous alcohol solvent. The ester of Formula VI is made from methyl pyruvate as described in *J. Org. Chem.*, (1983), 48, 158 (scheme 3)

Scheme 3

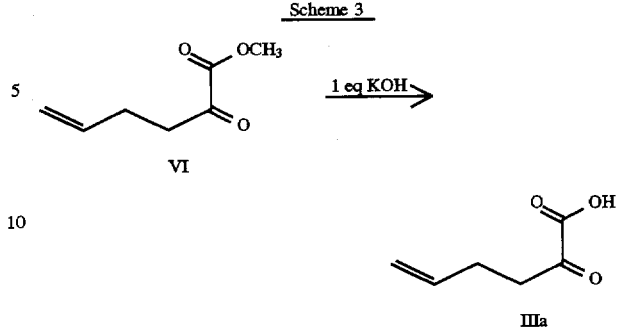

The triazolinone of Formula IIa can be made by the method described in Scheme 2. The hydrazone of Formula Va (compound of Formula V wherein $R^2$ is H) is made by treating 2-oxo-5-hexanoic acid IIIa with a phenyl hydrazine of Formula IV under acidic conditions using hydrochloric acid in an organic solvent such as ethyl or methyl alcohol at a temperature between room temperature and about 100° C. Schmidt rearrangement of hydrazone of Formula Va using an azide such as diphenylphosphoryl azide followed by intramolecular cyclization at a temperature between about 0° C. and about 100° C. affords the intermediate of Formula IIa.

Treatment of the olefin of Formula II with MCPBA (m-chloroperoxybenzoic acid) in an inert solvent such as dichloromethane at a temperature between about 0° C. and about 100° C., preferably at room temperature, gives an epoxide of Formula VII (Scheme 4). Intramolecular cyclization of the epoxide using a base such as potassium carbonate in an inert solvent such as acetonitrile or acetone gives the 6-membered ring product of Formula Ic (compound of Formula I wherein $R^1$ is 6-OH). Fluorination of the alcohol of Formula Ic with DAST (diethylaminosulfur trifluoride) at a temperature between about −78° C. and about 100° C. in an inert solvent such as dichloromethane gives the fluorinated product of Formula Id.

Scheme 4

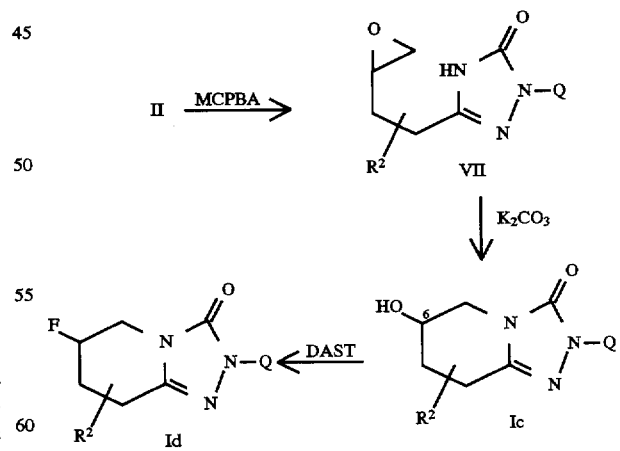

The alcohol of Formula Ic can also be prepared by hydroxybromination of the olefin of Formula II using N-bromosuccinimide (NBS) and water or N-bromoacetamide and water followed by cyclization of the resulting bromohydrin of Formula VIII using potassium carbonate in an inert solvent such as acetonitrile or acetone (Scheme 5).

Scheme 5

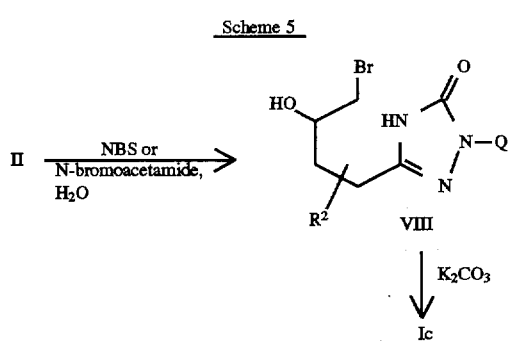

Compounds of Formula Ic can also be convened to the chloro-, bromo-, and iodo-$R^1$ substituted bicyclic triazolinones of Formula I using methods known to those skilled in the art. The hydroxy group in compounds of Formula Ic can be acylated by known methods to prepare the alkylcarbonyloxy and haloalkylcarbonyloxy derivatives. In addition, the hydroxy or halo group can be convened by known methods to afford the $R^1$=alkoxy and haloalkoxy derivatives (March, J., Advanced Organic Chemistry, (1992), 4th Ed., John Wiley and Sons, Inc., pp 386–389). In fact all the $R^1$=OH or halogen compounds in the following Schemes can be functionalized as is known in the art to prepare the other $R^1$ substituted compounds. Compounds wherein $R^1$ and $R^2$ are taken together along with the carbon atom to which they are attached to form C=O can be prepared from the corresponding $R^1$=OH and $R^2$=H compounds by well-known methods for oxidizing secondary alcohols to ketones.

Compounds of Formulae Ie and If (compounds of Formula I wherein n is 1) can be prepared as illustrated in Scheme 6. Oxidative cleavage of the olefin of Formula II using sodium periodate and a catalytic amount of osmium tetroxide in an inert solvent mixture such as tetrahydrofuran (THF) and water, or using ozone in dichloromethane followed by reductive workup using dimethyl sulfide (DMS), affords the aldehyde of Formula IX. Intramolecular cyclization of the aldehyde under basic conditions using potassium carbonate or sodium hydride gives the 5-membered ring alcohol of Formula Ie. Treatment of the alcohol of Formula Ie with DAST in an inert solvent such as dichloromethane at a temperature between about −80° C. and about 60° C. produces the fluoride of Formula If. The fluoride If can also be made by direct cyclization and fluorination using DAST at a temperature range between about −100° C. and about 60° C.

Scheme 6

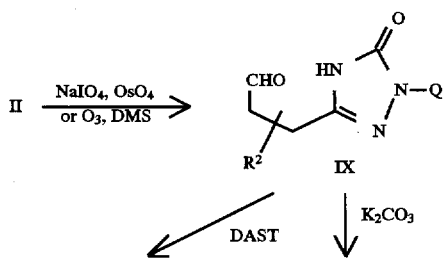

-continued
Scheme 6

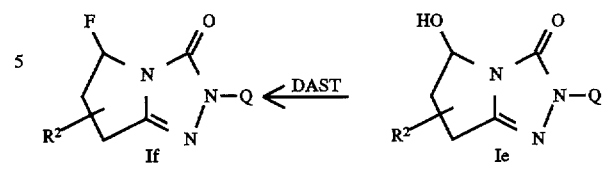

Hydroboration of the olefin of Formula II with 9-borabicyclo[3.3.1]nonane (9-BBN) gives the alcohol of Formula X after oxidative workup (Scheme 7). Oxidation of alcohol X with oxidizing agents such as PDC (pyridinium dichlorochromate) produces the hemiaminal of Formula Ig presumably via the aldehyde intermediate of Formula XI. The fluoro compound of Formula Ih can be made by the treatment of the hemiaminal with DAST.

Scheme 7

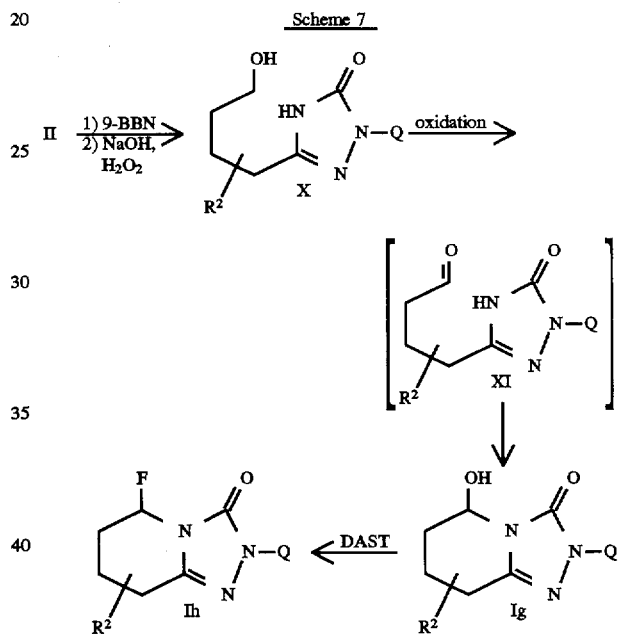

Triazolinones of Formula XII can be made from 2-oxo4-pentenoic acids and sustituted phenyl hydrazines of Formula IV by methods known to those skilled in the art and the methods taught herein (Scheme 8). The epoxide of Formula XIII can be prepared from the olefin of Formula XII using an oxidant such as MCPBA. Intramolecular cyclization of the epoxide with a base such as potassium carbonate affords the alcohol of Formula Ii. The fluoro compound of Formula Ij can be made from the alcohol using DAST at a temperature between about −70° C. and about room temperature in an inert solvent such as dichloromethane.

Scheme 8

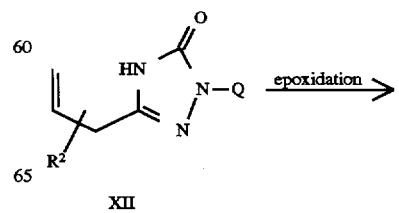

11
-continued
Scheme 8

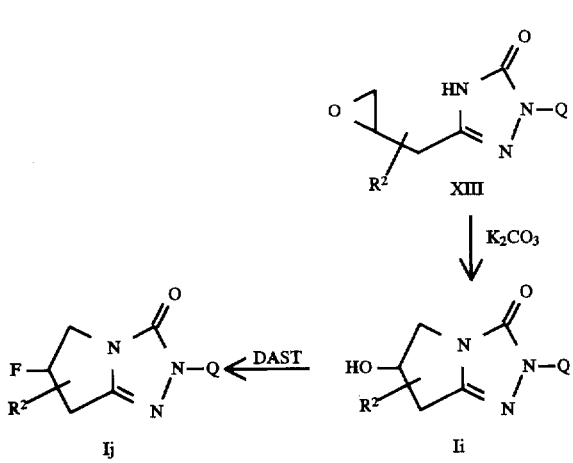

Compounds of Formula Iq can be prepared from the unsubstituted compounds of Formula XIV as illustrated in Scheme 9. Treatment of the bicyclic triazolinone of Formula XIV with N-bromosuccinimide (NBS) under allylic bromination conditions affords the mono-bromo derivative of Formula Io. One skilled in the art will recognize that bromination may also occur on Q if an electron-rich phenyl ring is present. When Q is Q-1, we have found that bromination does not occur on the phenyl ring when $R^3$ and $R^5$ are Cl and $R^4$ is acetyloxy. The acetyl group can be removed by known methods, and the liberated phenolic hydroxyl group can be functionalized by known methods to prepare the desired $OR^9$ group.

Hydrolysis of the bromide in hot aqueous dimethyl sulfoxide (DMSO) affords the alcohol of Formula Ip. The fluoro compound of Formula Iq can be prepared by treatment of the alcohol with diethylaminosulfur trifluoride (DAST) as described above.

Scheme 9

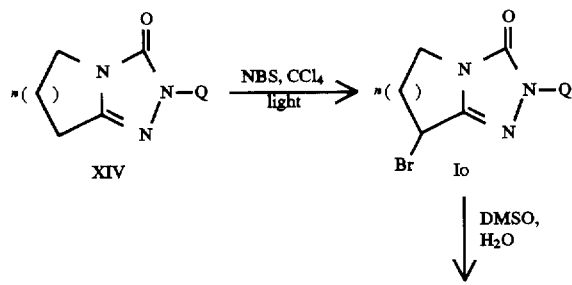

12
-continued
Scheme 9

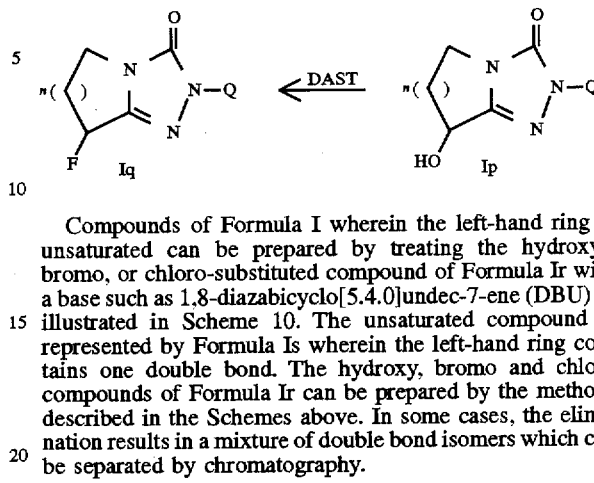

Compounds of Formula I wherein the left-hand ring is unsaturated can be prepared by treating the hydroxy-, bromo, or chloro-substituted compound of Formula Ir with a base such as 1,8-diazabicyclo[5.4.0]undec-7-ene (DBU) as illustrated in Scheme 10. The unsaturated compound is represented by Formula Is wherein the left-hand ring contains one double bond. The hydroxy, bromo and chloro compounds of Formula Ir can be prepared by the methods described in the Schemes above. In some cases, the elimination results in a mixture of double bond isomers which can be separated by chromatography.

Scheme 10

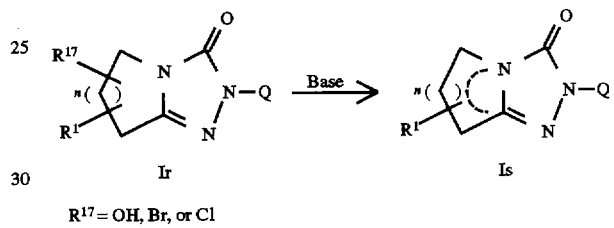

$R^{17}$ = OH, Br, or Cl

Compounds of Formula I wherein $R^1$ and $R^2$ are taken together along with the carbon atoms to which they are attached to form an epoxide can be prepared from the corresponding unsaturated ring compound of Formula Is by well known methods for epoxidizing double bonds, for example using MCPBA in $CH_2Cl_2$.

Compounds of Formula It can be prepared as illustrated in Scheme 11. Allylic oxidation of the terminal alkene of Formula II with t-butyl hydroperoxide and catalytic selenium (IV) oxide in an inert solvent such as dichloromethane produces the allylic alcohol of Formula XV. Protection of the secondary alcohol as the t-butyldimethylsilyl (TBS) ether is accomplished using t-butylchlorodimethylsilane and a base, preferably triethylamine and catalytic 4-(dimethylamino)pyridine. The terminal olefin is converted to the primary alcohol to afford compounds of Formula XVI using 9-BBN followed by treatment with sodium perborate. Ring cyclization is accomplished using the Martin sulfurane dehydrating agent $[C_6H_5(CF_3)_2O]_2S(C_6H_5)_2$. Removal of the TBS group and liberation of the alcohol can be accomplished using tetrabutylammonium fluoride. The alcohol can be converted to the corresponding fluoro compound using DAST, or to other $R^1$ substituted compounds as described above.

Scheme 11

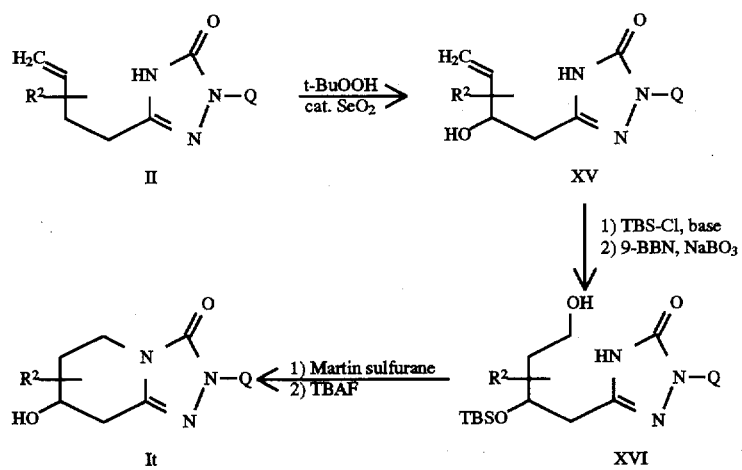

For some compounds of Formula I wherein $R^2$ is other than hydrogen, the $R^2$ substituent is more conveniently introduced after cyclization to form the bicyclic triazolinone. This is especially the case when $R^1$ and $R^2$ are attached to the same carbon atom.

EXAMPLE 1

Step 1

Preparation of 2-oxo-5-hexenoic acid, 2,4-dichloro-5-[(2-propynyl)oxy]-phenylhydrazone.

To a solution of 2.0 g (14.1 mmol) of methyl 2-oxo-5-hexanoate prepared as described in *J. Org. Chem.*, (1983), 48, 158, in 2.5 mL of ethyl alcohol was added a solution of 788 mg (14.1 mmol) of potassium hydroxide in 2.5 mL of water in an ice bath. After 10 min, a mixture of 20 mL of 10% aqueous hydrochloric acid and 20 mL of ethyl alcohol and 3.25 g (14.0 mmol) of 2,4-dichloro-5-[(2-propynyl)oxy] phenylhydrazine were added in sequence. The mixture was then warmed at 40° C. for 1h. The mixture was cooled to room temperature and filtered to give 3.78 g of the title product of Step 1 as a brown solid, m.p.: 152°–153° C.; $^1$H NMR (DMSO-$d_6$, 400 MHz) δ 12.5 (s,1H), 7.6 (s,1H), 7.4 (s,1H), 5.9 (m,1H), 4.9–5.1 (m,2H), 4.9 (s,2H) 3.7 (s,1H), 2.6 (t,2H), 2.4 (q,2H).

Step 2

Preparation of 2-[2,4-dichloro-5-(2-propynyloxy) phenyl]-2,4-dihydro-5-(3-butenyl)-3H- 1,2,4-triazol-3-one To a solution of 7.34 g (21.6 mmol) of 2-oxo-5-hexenoic acid, 2,4-dichloro-5-[(2-propynyl)oxyl]phenylhydrazone in 100 mL of toluene was added 6.54 g (23.7 mmol) of diphenylphosphoryl azide and 3.6 mL of triethylamine (25.9 mmol) in sequence. The reaction mixture was then warmed at reflux for 1h. The mixture was cooled to room temperature and the excess toluene and triethylamine were evaporated in vacuo. The crude product was purified by flash chromatography over silica gel, eluting with 95:5 v:v mixture of dichloromethane and methanol to give 6.64 g of the title compound of Step 2 as a brown solid, m.p.: 150°–151° C.; $^1$H NMR (CDCl$_3$, 400 MHz) δ 11.7 (broad s,1H), 7.6 (s,1H), 7.2 (s,1H), 5.95–5.7 (m,1H), 5.2–5.0 (m,2H), 4.8 (s,2H), 2.7 (t,2) 2.6 (t,1H), 2.5 (q,2H).

Step 3

Preparation of 2-[2,4-dichloro-5-(2-propynyloxy) phenyl]-2,4-dihydro-5-(3.4epoxybutyl)-3H- 1,2,4-triazol-3-one To a solution of 500 mg (1.48 mmol) of 2-[2,4-dichloro-5-(2-propynyloxy)-phenyl]-2,4-dihydro-5-(3-butenyl)-3H-1,2,4-triazol-3-one in 20 mL of dichloromethane was added 172 mg (1.63 mmol) of sodium carbonate and 970 mg of m-chloroperoxybenzoic acid (50–60%, 2.81 mmol) in an ice bath. The reaction mixture was stirred at room temperature for 24h. The mixture was filtered and the filtrate was evaporated in vacuo to give 500 mg of the title compound of Step 3 as yellow solid. The crude product was used in the following reaction without further purification. $^1$H NMR (CDCl$_3$, 400 MHz) δ 11.25 (s,1H), 7.55 (s,1H), 7.2 (s,1H), 4.8 (s,2H), 3.05 (m,1H), 2.8 (t,1H), 2.8 (t,2H), 2.6 (s,1H), 2.75 (d,1H), 2.2 (m,1H), 1.8 (m,1H).

Step 4

Preparation of 5,6,7,8-tetrahydro-2-[2,4-dichloro-5-(2-propynyloxy)phenyl]-6-hydroxy- 1,2,4-triazolo[4.3-α]pyridin-3(2H)-one A mixture of 500 mg (1.41 mmol) of 2-[2,4-dichloro-5-(2-propynyloxy)-phenyl]-2,4-dihydro-5-(3,4-epoxybutyl)-3H-1,2,4-triazol-3-one and 563 mg (4.08 mmol) of potassium carbonate in 20 mL of acetonitrile was warmed at reflux for 2h. The mixture was cooled to room temperature and filtered. The filtrate was evaporated in vacuo. The crude product was purified by flash chromatography over silica gel, eluting with a 95:5 v:v mixture of dichloromethane and methanol to give 184 mg of the title product of Step 4 as a pale yellow foam, $^1$H NMR (CDCl$_3$, 400 MHz) δ 7.5 (s,1H), 7.15 (s,1H), 4.8 (s,2H), 4.45 (broad t,1H), 3.8 (m,2H), 3.0 (m,1H), 2.8 (m,1H), 2.6 (s,1H), 2.2 (s,1H), 2.15 (m,1H), 1.95 (m,1H).

EXAMPLE 2

Step 1

Preparation of 2-[2,4-dichloro-5-(2-propynyloxy) phenyl]-2,4-dihydro-5-(4-bromo-3-hydroxybutyl )-3H- 1,2,4-triazol-3-one To a solution of 200 mg (0.592 mmol) of 2-[2,4-dichloro-5-(2-propynyloxy)phenyl]-2,4-dihydro-5-(3-butenyl)-3H-1, 2,4-triazol-3-one in 1.8 mL of dimethyl sulfoxide was added 30 mL (1.67 mmol) of water and 211 mg (1.18 mmol) of N-bromosuccinimide, in sequence, at room temperature. The mixture was stirred at room temperature for 10 min. The mixture was then poured into cold water and extracted with dichloromethane. The organic layer was dried (MgSO$_4$) and concentrated in vacuo. The crude product was purified by flash chromatography over silica gel, eluting with a 97:3 v:v mixture of dichloromethane and methanol to give 200 mg of the title product of Step 1 as a pale yellow foam. $^1$H NMR (CDCl$_3$, 400 MHz) δ 11.0 (s, 1H), 7.55 (s,1H), 7.15 (s,1H), 4.8 (s,2H), 3.8 (m,1H), 3.4 (m,2H), 2.8 (m,2H), 2.6 (t,1H), 2.1–1.8 (m,2H).

Step 2

Preparation of 5,6,7,8-tetrahydro-2-[2,4,-dichloro-5-(2-propynyloxy)phenyl]- 6-hydroxy-2,4-triazolo[4,3-α]pyridin-3(2H)-one A mixture of 200 mg (0.460 mmol) of 2-[2,4-dichloro-5-(2-propynyloxy)-phenyl]-2,4-dihydro-5-(4-bromo-3-hydroxybutyl)-3H- 1,2,4-triazol-3-one and 127 mg (0.920 mmol) of potassium carbonate in 10 mL of acetonitrile was warmed at reflux for 2h. The mixture was cooled to room temperature and filtered. The filtrate was evaporated in vacuo. The crude product was purified by flash chromatography over silica gel, eluting with a 96:4 v:v mixture of dichloromethane and methanol to give 57 mg of the title product as a pale yellow foam. The $^1$H NMR spectrum of the product was identical to that obtained for the product of Step 4 in Example 1.

EXAMPLE 3

Preparation of 5,6,7,8 tetrahydro-2-[2,4-dichloro-5-(2-propynyloxy)phenyl]-6-fluoro-1,2,4-triazolo[4,3-α]pyridin-3(2H)-one To a solution of 169 mg (0.477 mmol) of 5,6,7,8-tetrahydro-2-[2,4-dichloro-5-(2-propynyloxy)phenyl]-6-hydroxy-1,2,4-triazolo[4,3-a]pyridin-3(2H)-one in 5 mL of dichloromethane was added 76 μl (0.573 mmol) of diethylaminosulfur trifluoride (DAST) at 0° C. The reaction mixture was stirred at 0° C. for 1h. The mixture was then quenched with ice and extracted with dichloromethane. The organic extracts were dried (MgSO$_4$), and then concentrated in vacuo to give a pale red solid. The crude product was purified by flash chromatography over silica gel, eluting with a 95:5 v:v mixture of dichloromethane and methanol to give 64 mg of the title product as a pale yellow foam. $^{19}$F NMR (CDCl$_3$, 400 MHz) δ-188 ppm, $^1$H NMR (CDCl$_3$, 400 MHz) δ 7.5 (s,1H), 7.1 (s,1H), 5.2 (m,1H), 4.8 (s,2H), 4.2–3.6 (m,2H), 3.2–3.0 (m,1H), 3.0–2.6 (m,1H), 2.5 (s,1H), 2.3–1.8 (m,2H).

EXAMPLE 4

Step 1

Preparation of 2-[2,4-dichloro-5-(2-propynyloxy) phenyl]-2,4-dihydro-5-(3-oxo-propyl)-3H-1,2,4-triazol-3-one To a solution of 500 mg (1.48 mmol) of 2-[2,4-dichloro-5-(2-propynyloxy)phenyl]-2,4-dihydro-5-(3-butenyl)-3H-1,2,4-triazol-3-one in a mixture of 10 mL of tetrahydrofuran and 10 mL of water was added 696 mg (3.25 mmol) of sodium periodate and 167 mL of 0.18M aqueous solution of osmium tetroxide at room temperature. The mixture was stirred at the room temperature for 2h, and then diluted with water and extracted with ethyl acetate. The organic layer was dried (MgSO$_4$) and concentrated in vacuo. The crude product was purified by flash chromatography over silica gel, eluting with a 96:4 v:v mixture of dichloromethane and methanol to give 464 mg of the title product of Step 1 as a white foam. $^1$H NMR (CDCl$_3$, 400 MHz) δ 11.5 (broad s,1H), 9.8 (s,1H), 7.55 (s,1H), 7.2 (s,1H), 4.8 (s,2H), 2.9 (m,4H).

Step 2

Preparation of 2,5,6,7-tetrahydro-2-[2,4-dichloro-(2-propynyloxy)phenyl]-5-fluoro-3H-pyrrolo[2,1-c]-1,2,4-triazol-3-one To a solution of 40 mg (0.117 mmol) of 2-[2,4-dichloro-5-(2-propynyloxy)phenyl]-2,4-dihydro-5-(3-oxo-propyl)-3H-1,2,4-triazol-3-one in 5 mL of dichloromethane was added 22.7 mg (0.141 mmol) of diethylaminosulfur trifluoride at 0° C. The mixture was stirred at room temperature for 30 minutes, and then quenched with cold water and extracted with dichloromethane. The organic layer was washed with brine and water, dried (MgSO$_4$) and concentrated in vacuo. The crude product was purified by flash chromatography over silica gel, eluting with a 95:5 v:v mixture of dichloromethane and methanol to give 18 mg of 2-[2,4-dichloro-5-(2-propynyloxy)phenyl]-2,4-dihydro-5-(3,3-difluoropropyl)-3H-1,2,4-triazol-3-one as a white foam $^1$H NMR (CDCl$_3$, 400 MHz) δ 12.0 (s,1H), 7.55 (s,1H), 7.2 (s,1H), 5.95 (t,1H, J=55 Hz), 4.8 (s,2H), 2.8 (t,2H), 2.6 (s,1H), 2.3 (m,2H), and 7 mg of the title product as a solid, $^1$H NMR (CDCl$_3$, 400 MHz) δ 7.5 (s,1H), 7.2 (s,1H), 6.4 and 6.2 (q,1H, J=60 and 5 Hz), 4.8 (s,2H), 3.15 (m,1H), 3.0–2.6 (m,3H), 2.6 (s,1H).

EXAMPLE 5

Step 1

Preparation of 5,6,7,8-tetrahydro-2-(5-acetyloxy-2,4-dichlorophenyl)-8-bromo1,2,4-triazolo[4,3-α]pyridin-3(2H)-one To a solution of 3.55 g (10.4 mmol) of 5,6,7,8-tetrahydro-2-(5-acetyloxy-2,4-dichlorophenyl)-1,2,4-triazolo[4,3-α]pyridin-3(2H)-one in 100 mL of carbon tetrachloride was added 2.03 g (11.4 mmol) of N-bromosuccinimide at room temperature. The mixture was warmed under reflux by irradiating with a sun lamp for 3h. The mixture was cooled to room temperature and concentrated under reduced pressure. The crude product was purified by flash chromatography over silica gel, eluting with a 1:1 v:v mixture of ethyl acetate and n-hexane to give 4.10 g of the title product of Step 1 as a white solid, m.p.: 75°–83° C.; $^1$H NMR (CDCl$_3$, 300 MHz) δ 7.6 (s,1H), 7.35 (s,1H), 5.25 (m,1H), 4.0 (m,1H), 3.6 (m,1H), 2.75 (s,3H), 2.5–1.9 (m,4H).

Step 2

Preparation of 5,6,7,8-tetrahydro-2-(2,4-dichloro-5-hydroxyphenyl)-8-hydroxy-1,2,4-triazolo[4,3-α]pyridin-3(2H)-one A mixture of 4.10 g (9.74 mmol) of 5,6,7,8-tetrahydro-2-(5-acetyloxy-2,4-dichlorophenyl)-8-bromo-1,2,4-triazolo[4,3-α]pyridin-3 (2H)-one, 50 mL of DMSO, and 50 mL of water was warmed at 90° C. for 5h. The mixture was cooled to room temperature and diluted with ethyl acetate. The organic layer was washed with water, dried (MgSO$_4$) and concentrated under reduced pressure. The crude product was purified by flash chromatography over silica gel, eluting with a 95:5 v:v mixture of dichloromethane and methanol to give 1.70 g of the title product of Step 2 as a yellow oil. $^1$H NMR (CD$_3$SO, 300 MHz) δ 7.65 (s,1H), 7.05 (s,1H), 5.85 (br s,1H), 4.60 (m,1H), 3.6–3.4 (m,2H), 2.2–1.8 (m,4H).

Step 3

Preparation of 5,6,7,8-tetrahydro-2-[-2,4-dichloro-5-(2-propynyloxy)phenyl]-8-hydroxy-1,2,4-triazolo[4,3-α]pyridin-3(2H)-one A mixture of 1.7 g (5.38 mmol) of 5,6,7,8-tetrahydro-2-(2,4-dichloro-5-hydroxyphenyl)-8-hydroxy-,1,2,4-triazolo[4,3-α]pyridin-3(2H)-one, 959 mL (10.7 mmol) of propargyl bromide (80% in toluene), and 1.48 g (10.7 mmol) of potassium carbonate in 20 mL of acetonitrile was warmed at reflux for 5h. The mixture was cooled to room temperature and filtered. The filtrate was evaporated under reduced pressure. The crude product was flash chromatographed over silica gel, eluting with a 97:3 v:v mixture of dichloromethane and methanol to give 1.36 g of the title product of Step 3 as a yellow solid, m.p. 168°–170° C.; $^1$H NMR (CDCl$_3$, 300 MHz) δ 7.55 (s,1H), 7.15 (s,1H), 4.85 (m,1H), 4.8 (d,2H), 3.8–3.6 (m,2H), 2.6 (m,1H), 2.55 (s,1H), 2.6 (m,1H), 2.55 (s,1H), 2.3–1.9 (m,4H).

Step 4

Preparation of 5,6,7,8-tetrahydro-2-[2,4-dichloro-5-(2-propynyloxy)phenyl]-8-fluoro-1,2,4-triazolo[4,3-α]pyridin-3(2H)-one To a solution of 300 mg (0.847 mmol) of 5,6,7,8-tetrahydro-2-[2,4-dichloro-5-(2-propynyloxy)phenyl]-8-hydroxy-1,2,4-triazolo[4,3-α]pyridin-3(2H)-one in 10 mL of dichloromethane was added 123 mL (0.930 mmol) of diethylaminosulfur trifluoride (DAST) at −78° C. The reaction mixture was stirred at −78° C. for 4h. The mixture was warmed to room temperature, quenched with ice, and extracted with dichloromethane. The organic layers were dried (MgSO$_4$), and concentrated under reduced pressure. The crude product was flash chromatographed over silica gel, eluting with a 98:2 v:v mixture of dichloromethane and methanol to give 272 mg of the title product of Step 4 as a yellow solid. $^{19}$F NMR (CDCl$_3$, 300 MHz) δ-172; $^1$H NMR (CDCl$_3$, 300 MHz) δ 7.55 (s,1H), 7.2 (s,1H), 5.6, 5.5 (2m, J=70 Hz,1H), 4.8 (s,2H), 4.0 (m,1H), 3.55 (m,1H), 2.6 (m,1H), 2.5–1.8 (m,4H).

Using the procedures outlined in Schemes 1–11, the compounds of Tables 1–6 can be prepared.

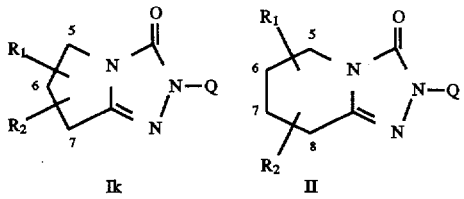

The following abbreviations are used in the tables which follow.

n = normal   Ph = phenyl   Me = methyl   i = iso   Pr = propyl

TABLE 1

Compounds of Formula Ik wherein Q = Q-1; R$^5$ = Cl

| R$^1$ | R$^2$ | R$^3$ | R$^4$ | R$^1$ | R$^2$ | R$^3$ | R$^4$ |
|---|---|---|---|---|---|---|---|
| 5-F | H | Cl | OCH$_2$C≡CH | 5-F | H | Cl | OCH(CH$_3$)C≡CH |
| 6-F | H | Cl | OCH$_2$C≡CH | 6-F | H | Cl | OCH(CH$_3$)C≡CH |
| 7-F | H | Cl | OCH$_2$C≡CH | 7-F | H | Cl | OCH(CH$_3$)C≡CH |
| 5-F | 5-F | Cl | OCH$_2$C≡CH | 5-F | 5-F | Cl | OCH(CH$_3$)C≡CH |
| 6-F | 6-F | Cl | OCH$_2$C≡CH | 6-F | 6-F | Cl | OCH(CH$_3$)C≡CH |
| 7-F | 7-F | Cl | OCH$_2$C≡CH | 7-F | 7-F | Cl | OCH(CH$_3$)C≡CH |
| 5-F | 6-F | Cl | OCH$_2$C≡CH | 5-F | 6-F | Cl | OCH(CH$_3$)C≡CH |
| 7-F | 6-F | Cl | OCH$_2$C≡CH | 7-F | 6-F | Cl | OCH(CH$_3$)C≡CH |
| 5-F | H | F | OCH$_2$C≡CH | 5-F | H | F | OCH(CH$_3$)C≡CH |
| 6-F | H | F | OCH$_2$C≡CH | 6-F | H | F | OCH(CH$_3$)C≡CH |
| 7-F | H | F | OCH$_2$C≡CH | 7-F | H | F | OCH(CH$_3$)C≡CH |
| 5-F | 5-F | F | OCH$_2$C≡CH | 5-F | 5-F | F | OCH(CH$_3$)C≡CH |
| 6-F | 6-F | F | OCH$_2$C≡CH | 6-F | 6-F | F | OCH(CH$_3$)C≡CH |
| 7-F | 7-F | F | OCH$_2$C≡CH | 7-F | 7-F | F | OCH(CH$_3$)C≡CH |
| 5-F | 6-F | F | OCH$_2$C≡CH | 5-F | 6-F | F | OCH(CH$_3$)C≡CH |
| 7-F | 6-F | F | OCH$_2$C≡CH | 7-F | 6-F | F | OCH(CH$_3$)C≡CH |
| 5-F | H | Cl | OCH(CH$_3$)$_2$ | 5-F | H | Cl | OCH$_2$CH=CH$_2$ |
| 6-F | H | Cl | OCH(CH$_3$)$_2$ | 6-F | H | Cl | OCH$_2$CH=CH$_2$ |
| 7-F | H | Cl | OCH(CH$_3$)$_2$ | 7-F | H | Cl | OCH$_2$CH=CH$_2$ |
| 5-F | 5-F | Cl | OCH(CH$_3$)$_2$ | 5-F | 5-F | Cl | OCH$_2$CH=CH$_2$ |
| 6-F | 6-F | Cl | OCH(CH$_3$)$_2$ | 6-F | 6-F | Cl | OCH$_2$CH=CH$_2$ |
| 7-F | 7-F | Cl | OCH(CH$_3$)$_2$ | 7-F | 7-F | Cl | OCH$_2$CH=CH$_2$ |
| 5-F | 6-F | Cl | OCH(CH$_3$)$_2$ | 5-F | 6-F | Cl | OCH$_2$CH=CH$_2$ |
| 7-F | 6-F | Cl | OCH(CH$_3$)$_2$ | 7-F | 6-F | Cl | OCH$_2$CH=CH$_2$ |
| 5-Cl | H | Cl | OCH$_2$C≡CH | 5-Cl | H | Cl | OCH(CH$_3$)C≡CH |
| 6-Cl | H | Cl | OCH$_2$C≡CH | 6-Cl | H | Cl | OCH(CH$_3$)C≡CH |
| 7-Cl | H | Cl | OCH$_2$C≡CH | 7-Cl | H | Cl | OCH(CH$_3$)C≡CH |
| 5-Cl | 5-Cl | Cl | OCH$_2$C≡CH | 5-Cl | 5-Cl | Cl | OCH(CH$_3$)C≡CH |

TABLE 1-continued

| | | | | | | | |
|---|---|---|---|---|---|---|---|
| 6-Cl | 6-Cl | Cl | OCH₂C≡CH | 6-Cl | 6-Cl | Cl | OCH(CH₃)C≡CH |
| 7-Cl | 7-Cl | Cl | OCH₂C≡CH | 7-Cl | 7-Cl | Cl | OCH(CH₃)C≡CH |
| 5-Cl | 6-Cl | Cl | OCH₂C≡CH | 5-Cl | 6-Cl | Cl | OCH(CH₃)C≡CH |
| 7-Cl | 6-Cl | Cl | OCH₂C≡CH | 7-Cl | 6-Cl | Cl | OCH(CH₃)C≡CH |
| 5-Cl | H | F | OCH₂C≡CH | 5-Cl | H | F | OCH(CH₃)C≡CH |
| 6-Cl | H | F | OCH₂C≡CH | 6-Cl | H | F | OCH(CH₃)C≡CH |
| 7-Cl | H | F | OCH₂C≡CH | 7-Cl | H | F | OCH(CH₃)C≡CH |
| 5-Cl | 5-Cl | F | OCH₂C≡CH | 5-Cl | 5-Cl | F | OCH(CH₃)C≡CH |
| 6-Cl | 6-Cl | F | OCH₂C≡CH | 6-Cl | 6-Cl | F | OCH(CH₃)C≡CH |
| 7-Cl | 7-Cl | F | OCH₂C≡CH | 7-Cl | 7-Cl | F | OCH(CH₃)C≡CH |
| 5-Cl | 6-Cl | F | OCH₂C≡CH | 5-Cl | 6-Cl | F | OCH(CH₃)C≡CH |
| 7-Cl | 6-Cl | F | OCH₂C≡CH | 7-Cl | 6-Cl | F | OCH(CH₃)C≡CH |
| 5-Cl | H | Cl | OCH(CH₃)₂ | 5-Cl | H | Cl | OCH₂CH=CH₂ |
| 6-Cl | H | Cl | OCH(CH₃)₂ | 6-Cl | H | Cl | OCH₂CH=CH₂ |
| 7-Cl | H | Cl | OCH(CH₃)₂ | 7-Cl | H | Cl | OCH₂CH=CH₂ |
| 5-Cl | 5-Cl | Cl | OCH(CH₃)₂ | 5-Cl | 5-Cl | Cl | OCH₂CH=CH₂ |
| 6-Cl | 6-Cl | Cl | OCH(CH₃)₂ | 6-Cl | 6-Cl | Cl | OCH₂CH=CH₂ |
| 7-Cl | 7-Cl | Cl | OCH(CH₃)₂ | 7-Cl | 7-Cl | Cl | OCH₂CH=CH₂ |
| 5-Cl | 6-Cl | Cl | OCH(CH₃)₂ | 5-Cl | 6-Cl | Cl | OCH₂CH=CH₂ |
| 7-Cl | 6-Cl | Cl | OCH(CH₃)₂ | 7-Cl | 6-Cl | Cl | OCH₂CH=CH₂ |

| R¹ | R² | R³ | R⁵ | R⁴ | R¹ | R² | R³ | R⁵ | R⁴ |
|---|---|---|---|---|---|---|---|---|---|
| 5-F | H | Cl | Br | OCH₂C≡CH | 5-Br | H | Cl | Cl | OCH₂C≡CH |
| 6-F | H | Cl | Br | OCH₂C≡CH | 6-Br | H | Cl | Cl | OCH₂C≡CH |
| 7-F | H | Cl | Br | OCH₂C≡CH | 7-Br | H | Cl | Cl | OCH₂C≡CH |
| 5-F | 5-F | Cl | Br | OCH₂C≡CH | 6-OMe | H | Cl | Cl | OCH₂C≡CH |
| 6-F | 6-F | Cl | Br | OCH₂C≡CH | 6-OCF₃ | H | Cl | Cl | OCH₂C≡CH |
| 7-F | 7-F | Cl | Br | OCH₂C≡CH | 6-MeCO | H | Cl | Cl | OCH₂C≡CH |
| 5-F | 6-F | Cl | Br | OCH₂C≡CH | 6-CF₃CO | H | Cl | Cl | OCH₂C≡CH |
| 7-F | 6-F | Cl | Br | OCH₂C≡CH | 5-F | 6-OH | Cl | Cl | OCH₂C≡CH |
| 6-carbonyl | | Cl | Cl | OCH₂C≡CH | 6-carbonyl | | Cl | Cl | OCH(CH₃)₂ |
| 5-F | H | Cl | Cl | OCF₂C≡CH | 5-F | H | F | Cl | OCF₂C≡CH |
| 6-F | H | Cl | Cl | OCF₂C≡CH | 6-F | H | F | Cl | OCF₂C≡CH |
| 7-F | H | Cl | Cl | OCF₂C≡CH | 7-F | H | F | Cl | OCF₂C≡CH |
| 5-F | 5-F | Cl | Cl | OCF₂C≡CH | 5-F | 5-F | F | Cl | OCF₂C≡CH |
| 6-F | 6-F | Cl | Cl | OCF₂C≡CH | 6-F | 6-F | F | Cl | OCF₂C≡CH |
| 7-F | 7-F | Cl | Cl | OCF₂C≡CH | 7-F | 7-F | F | Cl | OCF₂C≡CH |
| 5-F | 6-F | Cl | Cl | OCF₂C≡CH | 5-F | 6-F | F | Cl | OCF₂C≡CH |
| 7-F | 6-F | Cl | Cl | OCF₂C≡CH | 7-F | 6-F | F | Cl | OCF₂C≡CH |

Compounds of Formula II wherein Q = Q-1; R⁵ = Cl

| R¹ | R² | R³ | R⁴ | R¹ | R² | R³ | R⁴ |
|---|---|---|---|---|---|---|---|
| 5-F | H | Cl | OCH₂C≡CH | 5-F | H | Cl | OCH(CH₃)C≡CH |
| 6-F | H | Cl | OCH₂C≡CH | 6-F | H | Cl | OCH(CH₃)C≡CH |
| 7-F | H | Cl | OCH₂C≡CH | 7-F | H | Cl | OCH(CH₃)C≡CH |
| 8-F | H | Cl | OCH₂C≡CH | 8-F | H | Cl | OCH(CH₃)C≡CH |
| 5-F | 5-F | Cl | OCH₂C≡CH | 5-F | 5-F | Cl | OCH(CH₃)C≡CH |
| 6-F | 6-F | Cl | OCH₂C≡CH | 6-F | 6-F | Cl | OCH(CH₃)C≡CH |
| 7-F | 7-F | Cl | OCH₂C≡CH | 7-F | 7-F | Cl | OCH(CH₃)C≡CH |
| 8-F | 8-F | Cl | OCH₂C≡CH | 8-F | 8-F | Cl | OCH(CH₃)C≡CH |
| 5-F | 6-F | Cl | OCH₂C≡CH | 5-F | 6-F | Cl | OCH(CH₃)C≡CH |
| 6-F | 7-F | Cl | OCH₂C≡CH | 6-F | 7-F | Cl | OCH(CH₃)C≡CH |
| 8-F | 7-F | Cl | OCH₂C≡CH | 8-F | 7-F | Cl | OCH(CH₃)C≡CH |
| 5-F | H | F | OCH₂C≡CH | 5-F | H | F | OCH(CH₃)C≡CH |
| 6-F | H | F | OCH₂C≡CH | 6-F | H | F | OCH(CH₃)C≡CH |
| 7-F | H | F | OCH₂C≡CH | 7-F | H | F | OCH(CH₃)C≡CH |
| 8-F | H | F | OCH₂C≡CH | 8-F | H | F | OCH(CH₃)C≡CH |
| 5-F | 5-F | F | OCH₂C≡CH | 5-F | 5-F | F | OCH(CH₃)C≡CH |
| 6-F | 6-F | F | OCH₂C≡CH | 6-F | 6-F | F | OCH(CH₃)C≡CH |
| 7-F | 7-F | F | OCH₂C≡CH | 7-F | 7-F | F | OCH(CH₃)C≡CH |
| 8-F | 8-F | F | OCH₂C≡CH | 8-F | 8-F | F | OCH(CH₃)C≡CH |
| 5-F | 6-F | F | OCH₂C≡CH | 5-F | 6-F | F | OCH(CH₃)C≡CH |
| 6-F | 7-F | F | OCH₂C≡CH | 6-F | 7-F | F | OCH(CH₃)C≡CH |
| 8-F | 7-F | F | OCH₂C≡CH | 8-F | 7-F | F | OCH(CH₃)C≡CH |
| 5-F | H | Cl | OCH(CH₃)₂ | 5-F | H | Cl | OCH₂CH=CH₂ |
| 6-F | H | Cl | OCH(CH₃)₂ | 6-F | H | Cl | OCH₂CH=CH₂ |
| 7-F | H | Cl | OCH(CH₃)₂ | 7-F | H | Cl | OCH₂CH=CH₂ |
| 8-F | H | Cl | OCH(CH₃)₂ | 8-F | H | Cl | OCH₂CH=CH₂ |
| 5-F | 5-F | Cl | OCH(CH₃)₂ | 5-F | 5-F | Cl | OCH₂CH=CH₂ |
| 6-F | 6-F | Cl | OCH(CH₃)₂ | 6-F | 6-F | Cl | OCH₂CH=CH₂ |
| 7-F | 7-F | Cl | OCH(CH₃)₂ | 7-F | 7-F | Cl | OCH₂CH=CH₂ |
| 8-F | 8-F | Cl | OCH(CH₃)₂ | 8-F | 8-F | Cl | OCH₂CH=CH₂ |
| 5-F | 6-F | Cl | OCH(CH₃)₂ | 5-F | 6-F | Cl | OCH₂CH=CH₂ |
| 6-F | 7-F | Cl | OCH(CH₃)₂ | 6-F | 7-F | Cl | OCH₂CH=CH₂ |
| 8-F | 7-F | Cl | OCH(CH₃)₂ | 8-F | 7-F | Cl | OCH₂CH=CH₂ |
| 5-F | H | F | OCH(CH₃)₂ | 5-F | H | F | OCH₂CH=CH₂ |

TABLE 1-continued

| R¹ | R² | R³ | R⁴ | R¹ | R² | R³ | R⁴ |
|---|---|---|---|---|---|---|---|
| 6-F | H | F | OCH(CH₃)₂ | 6-F | H | F | OCH₂CH=CH₂ |
| 7-F | H | F | OCH(CH₃)₂ | 7-F | H | F | OCH₂CH=CH₂ |
| 8-F | H | F | OCH(CH₃)₂ | 8-F | H | F | OCH₂CH=CH₂ |
| 5-F | 5-F | F | OCH(CH₃)₂ | 5-F | 5-F | F | OCH₂CH=CH₂ |
| 6-F | 6-F | F | OCH(CH₃)₂ | 6-F | 6-F | F | OCH₂CH=CH₂ |
| 7-F | 7-F | F | OCH(CH₃)₂ | 7-F | 7-F | F | OCH₂CH=CH₂ |
| 8-F | 8-F | F | OCH(CH₃)₂ | 8-F | 8-F | F | OCH₂CH=CH₂ |
| 5-F | 6-F | F | OCH(CH₃)₂ | 5-F | 6-F | F | OCH₂CH=CH₂ |
| 6-F | 7-F | F | OCH(CH₃)₂ | 6-F | 7-F | F | OCH₂CH=CH₂ |
| 8-F | 7-F | F | OCH(CH₃)₂ | 8-F | 7-F | F | OCH₂CH=CH₂ |
| 5-Cl | H | F | OCH₂C≡CH | 5-Cl | H | F | OCH(CH₃)C≡CH |
| 6-Cl | H | F | OCH₂C≡CH | 6-Cl | H | F | OCH(CH₃)C≡CH |
| 7-Cl | H | F | OCH₂C≡CH | 7-Cl | H | F | OCH(CH₃)C≡CH |
| 8-Cl | H | F | OCH₂C≡CH | 8-Cl | H | F | OCH(CH₃)C≡CH |
| 5-Cl | 5-Cl | F | OCH₂C≡CH | 5-Cl | 5-Cl | F | OCH(CH₃)C≡CH |
| 6-Cl | 6-Cl | F | OCH₂C≡CH | 6-Cl | 6-Cl | F | OCH(CH₃)C≡CH |
| 7-Cl | 7-Cl | F | OCH₂C≡CH | 7-Cl | 7-Cl | F | OCH(CH₃)C≡CH |
| 8-Cl | 8-Cl | F | OCH₂C≡CH | 8-Cl | 8-Cl | F | OCH(CH₃)C≡CH |
| 5-Cl | 6-Cl | F | OCH₂C≡CH | 5-Cl | 6-Cl | F | OCH(CH₃)C≡CH |
| 6-Cl | 7-Cl | F | OCH₂C≡CH | 6-Cl | 7-Cl | F | OCH(CH₃)C≡CH |
| 8-Cl | 7-Cl | F | OCH₂C≡CH | 8-Cl | 7-Cl | F | OCH(CH₃)C≡CH |
| 5-Cl | H | Cl | OCH(CH₃)₂ | 5-Cl | H | Cl | OCH₂CH=CH₂ |
| 6-Cl | H | Cl | OCH(CH₃)₂ | 6-Cl | H | Cl | OCH₂CH=CH₂ |
| 7-Cl | H | Cl | OCH(CH₃)₂ | 7-Cl | H | Cl | OCH₂CH=CH₂ |
| 8-Cl | H | Cl | OCH(CH₃)₂ | 8-Cl | H | Cl | OCH₂CH=CH₂ |
| 5-Cl | 5-Cl | Cl | OCH(CH₃)₂ | 5-Cl | 5-Cl | Cl | OCH₂CH=CH₂ |
| 6-Cl | 6-Cl | Cl | OCH(CH₃)₂ | 6-Cl | 6-Cl | Cl | OCH₂CH=CH₂ |
| 7-Cl | 7-Cl | Cl | OCH(CH₃)₂ | 7-Cl | 7-Cl | Cl | OCH₂CH=CH₂ |
| 8-Cl | 8-Cl | Cl | OCH(CH₃)₂ | 8-Cl | 8-Cl | Cl | OCH₂CH=CH₂ |
| 5-Cl | 6-Cl | Cl | OCH(CH₃)₂ | 5-Cl | 6-Cl | Cl | OCH₂CH=CH₂ |
| 6-Cl | 7-Cl | Cl | OCH(CH₃)₂ | 6-Cl | 7-Cl | Cl | OCH₂CH=CH₂ |
| 8-Cl | 7-Cl | Cl | OCH(CH₃)₂ | 8-Cl | 7-Cl | Cl | OCH₂CH=CH₂ |

| R¹ | R² | R³ | R⁵ | R⁴ | R¹ | R² | R³ | R⁵ | R⁴ |
|---|---|---|---|---|---|---|---|---|---|
| 5-F | H | Cl | Br | OCH₂C≡CH | 5-Br | H | Cl | Cl | OCH₂C≡CH |
| 6-F | H | Cl | Br | OCH₂C≡CH | 6-Br | H | Cl | Cl | OCH₂C≡CH |
| 7-F | H | Cl | Br | OCH₂C≡CH | 7-Br | H | Cl | Cl | OCH₂C≡CH |
| 8-Br | H | Cl | Br | OCH₂C≡CH | 8-Br | H | Cl | Cl | OCH₂C≡CH |
| 6-F | 6-F | Cl | Br | OCH₂C≡CH | 6-OMe | H | Cl | Cl | OCH₂C≡CH |
| 7-F | 7-F | Cl | Br | OCH₂C≡CH | 7-OCF₃ | H | Cl | Cl | OCH₂C≡CH |
| 5-F | 6-F | Cl | Br | OCH₂C≡CH | 6-MeCO | H | Cl | Cl | OCH₂C≡CH |
| 6-F | 7-F | Cl | Br | OCH₂C≡CH | 6-CF₃CO | H | Cl | Cl | OCH₂C≡CH |
| 8-F | 7-F | Cl | Br | OCH₂C≡CH | 6-F | 7-OH | Cl | Cl | OCH₂C≡CH |
| 7-carbonyl | | Cl | Cl | OCH₂C≡CH | 7-carbonyl | | Cl | Cl | OCH(CH₃)₂ |
| 5-F | H | Cl | Cl | OCF₂C≡CH | 5-F | H | F | Cl | OCF₂C≡CH |
| 6-F | H | Cl | Cl | OCF₂C≡CH | 6-F | H | F | Cl | OCF₂C≡CH |
| 7-F | H | Cl | Cl | OCF₂C≡CH | 7-F | H | F | Cl | OCF₂C≡CH |
| 8-Br | H | Cl | Cl | OCF₂C≡CH | 8-Br | H | F | Cl | OCF₂C≡CH |
| 6-F | 6-F | Cl | Cl | OCF₂C≡CH | 6-F | 6-F | F | Cl | OCF₂C≡CH |
| 7-F | 7-F | Cl | Cl | OCF₂C≡CH | 7-F | 7-F | F | Cl | OCF₂C≡CH |
| 5-F | 6-F | Cl | Cl | OCF₂C≡CH | 5-F | 6-F | F | Cl | OCF₂C≡CH |
| 6-F | 7-F | Cl | Cl | OCF₂C≡CH | 6-F | 7-F | F | Cl | OCF₂C≡CH |
| 8-F | 7-F | Cl | Cl | OCF₂C≡CH | 8-F | 7-F | F | Cl | OCF₂C≡CH |

TABLE 2

Compounds of Formula Ik wherein Q = Q-2; R⁶ = H; W = O

| R¹ | R² | R³ | R⁵ | R⁷ | R¹ | R² | R³ | R⁵ | R⁷ | R¹ | R² | R³ | R⁵ | R⁷ | R¹ | R² | R³ | R⁵ | R⁷ |
|---|---|---|---|---|---|---|---|---|---|---|---|---|---|---|---|---|---|---|---|
| 5-F | H | Cl | Cl | Me | 5-F | H | F | Cl | Me | 5-Cl | 6-Cl | Cl | Cl | Me | 5-Cl | 6-Cl | F | Cl | Me |
| 6-F | H | Cl | Cl | Me | 6-F | H | F | Cl | Me | 7-Cl | 6-Cl | Cl | Cl | Me | 7-Cl | 6-Cl | F | Cl | Me |
| 7-F | H | Cl | Cl | Me | 7-F | H | F | Cl | Me | 5-F | H | Cl | Cl | Me | 5-F | H | F | Cl | Me |
| 5-F | 5-F | Cl | Cl | Me | 5-F | 5-F | F | Cl | Me | 6-F | H | Cl | Cl | Me | 6-F | H | F | Cl | Me |
| 6-F | 6-F | Cl | Cl | Me | 6-F | 6-F | F | Cl | Me | 7-F | H | Cl | Cl | Me | 7-F | H | F | Cl | Me |
| 7-F | 7-F | Cl | Cl | Me | 7-F | 7-F | F | Cl | Me | 8-F | H | Cl | Cl | Me | 8-F | H | F | Cl | Me |
| 5-F | 6-F | Cl | Cl | Me | 5-F | 6-F | F | Cl | Me | 5-F | 5-F | Cl | Cl | Me | 5-F | 5-F | F | Cl | Me |
| 7-F | 6-F | Cl | Cl | Me | 7-F | 6-F | F | Cl | Me | 6-F | 6-F | Cl | Cl | Me | 6-F | 6-F | F | Cl | Me |
| 5-Cl | H | Cl | Cl | Me | 5-Cl | H | F | Cl | Me | 7-F | 7-F | Cl | Cl | Me | 7-F | 7-F | F | Cl | Me |
| 6-Cl | H | Cl | Cl | Me | 6-Cl | H | F | Cl | Me | 8-F | 8-F | Cl | Cl | Me | 8-F | 8-F | F | Cl | Me |
| 7-Cl | H | Cl | Cl | Me | 7-Cl | H | F | Cl | Me | 5-F | 6-F | Cl | Cl | Me | 45-F | 6-F | F | Cl | Me |
| 5-Cl | 5-Cl | Cl | Cl | Me | 5-Cl | 5-Cl | F | Cl | Me | 6-F | 7-F | Cl | Cl | Me | 6-F | 7-F | F | Cl | Me |
| 6-Cl | 6-Cl | Cl | Cl | Me | 6-Cl | 6-Cl | F | Cl | Me | 8-F | 7-F | Cl | Cl | Me | 8-F | 7-F | F | Cl | Me |
| 7-Cl | 7-Cl | Cl | Cl | Me | 7-Cl | 7-Cl | F | Cl | Me | 5-Cl | H | Cl | Cl | Me | 5-Cl | H | F | Cl | Me |

TABLE 2-continued

Compounds of Formula Ik wherein Q = Q-2; $R^6$ = H; W = O

| $R^1$ | $R^2$ | $R^3$ | $R^5$ | $R^7$ | $R^1$ | $R^2$ | $R^3$ | $R^5$ | $R^7$ |
|---|---|---|---|---|---|---|---|---|---|
| 6-Cl | H | Cl | Cl | Me | 6-Cl | H | F | Cl | Me |
| 7-Cl | H | Cl | Cl | Me | 7-Cl | H | F | Cl | Me |
| 8-Cl | H | Cl | Cl | Me | 8-Cl | H | F | Cl | Me |
| 5-Cl | 5-Cl | Cl | Cl | Me | 5-Cl | 5-Cl | F | Cl | Me |
| 6-Cl | 6-Cl | Cl | Cl | Me | 6-Cl | 6-Cl | F | Cl | Me |
| 7-Cl | 7-Cl | Cl | Cl | Me | 7-Cl | 7-Cl | F | Cl | Me |
| 8-Cl | 8-Cl | Cl | Cl | Me | 8-Cl | 8-Cl | F | Cl | Me |
| 5-Cl | 6-Cl | Cl | Cl | Me | 5-Cl | 6-Cl | F | Cl | Me |
| 6-Cl | 7-Cl | Cl | Cl | Me | 6-Cl | 7-Cl | F | Cl | Me |
| 8-Cl | 7-Cl | Cl | Cl | Me | 8-Cl | 7-Cl | F | Cl | Me |

TABLE 3

| $R^1$ | $R^2$ | $R^3$ | $R^7$ | $R^8$ | $R^1$ | $R^2$ | $R^3$ | $R^7$ | $R^8$ |
|---|---|---|---|---|---|---|---|---|---|
| \multicolumn{10}{c}{Compounds of the formula Ik wherein Q = Q-6; W = O; $R^6$ = H} |
| 5-F | H | F | H | $CH_2C\equiv CH$ | 5-F | H | F | H | $CH(CH_3)C\equiv CH$ |
| 5-F | H | F | $CH_3$ | $CH_2C\equiv CH$ | 5-F | H | F | $CH_3$ | $CH(CH_3)C\equiv CH$ |
| 6-F | H | F | H | $CH_2C\equiv CH$ | 6-F | H | F | H | $CH(CH_3)C\equiv CH$ |
| 6-F | H | F | $CH_3$ | $CH_2C\equiv CH$ | 6-F | H | F | $CH_3$ | $CH(CH_3)C\equiv CH$ |
| 7-F | H | F | H | $CH_2C\equiv CH$ | 7-F | H | F | H | $CH(CH_3)C\equiv CH$ |
| 7-F | H | F | $CH_3$ | $CH_2C\equiv CH$ | 7-F | H | F | $CH_3$ | $CH(CH_3)C\equiv CH$ |
| 5-F | 5-F | F | H | $CH_2C\equiv CH$ | 5-F | 5-F | F | H | $CH(CH_3)C\equiv CH$ |
| 6-F | 6-F | F | H | $CH_2C\equiv CH$ | 6-F | 6-F | F | H | $CH(CH_3)C\equiv CH$ |
| 6-F | 6-F | F | $CH_3$ | $CH_2C\equiv CH$ | 6-F | 6-F | F | $CH_3$ | $CH(CH_3)C\equiv CH$ |
| 7-F | 7-F | F | H | $CH_2C\equiv CH$ | 7-F | 7-F | F | H | $CH(CH_3)C\equiv CH$ |
| 5-Cl | H | F | H | $C_2C\equiv CH$ | 5-Cl | H | F | H | $CH(CH_3)C\equiv CH$ |
| 5-Cl | H | F | $CH_3$ | $CH_2C\equiv CH$ | 5-Cl | H | F | $CH_3$ | $CH(CH_3)C\equiv CH$ |
| 6-Cl | H | F | H | $CH_2C\equiv CH$ | 6-Cl | H | F | H | $CH(CH_3)C\equiv CH$ |
| 6-Cl | H | F | $CH_3$ | $CH_2C\equiv CH$ | 6-Cl | H | F | $CH_3$ | $CH(CH_3)C\equiv CH$ |
| 7-Cl | H | F | H | $CH_2C\equiv CH$ | 7-Cl | H | F | H | $CH(CH_3)C\equiv CH$ |
| 7-Cl | H | F | $CH_3$ | $CH_2C\equiv CH$ | 7-Cl | H | F | $CH_3$ | $CH(CH_3)C\equiv CH$ |
| 5-Cl | 5-Cl | F | H | $CH_2C\equiv CH$ | 5-Cl | 5-Cl | F | H | $CH(CH_3)C\equiv CH$ |
| 6-Cl | 6-Cl | F | H | $CH_2C\equiv CH$ | 6-Cl | 6-Cl | F | H | $CH(CH_3)C\equiv CH$ |
| 6-Cl | 6-Cl | F | $CH_3$ | $CH_2C\equiv CH$ | 6-Cl | 6-Cl | F | $CH_3$ | $CH(CH_3)C\equiv CH$ |
| 7-Cl | 7-Cl | F | H | $CH_2C\equiv CH$ | 7-Cl | 7-Cl | F | H | $CH(CH_3)C\equiv CH$ |
| \multicolumn{10}{c}{Compounds of Formula II wherein Q = Q-6; W = O; $R^6$ = H} |
| 5-F | H | F | H | $CH_2C\equiv CH$ | 5-F | H | F | H | $CH(CH_3)C\equiv CH$ |
| 5-F | H | F | $CH_3$ | $CH_2C\equiv CH$ | 5-F | H | F | $CH_3$ | $CH(CH_3)C\equiv CH$ |
| 6-F | H | F | H | $CH_2C\equiv CH$ | 6-F | H | F | H | $CH(CH_3)C\equiv CH$ |
| 6-F | H | F | $CH_3$ | $CH_2C\equiv CH$ | 6-F | H | F | $CH_3$ | $CH(CH_3)C\equiv CH$ |
| 7-F | H | F | H | $CH_2C\equiv CH$ | 7-F | H | F | H | $CH(CH_3)C\equiv CH$ |
| 7-F | H | F | $CH_3$ | $CH_2C\equiv CH$ | 7-F | H | F | $CH_3$ | $CH(CH_3)C\equiv CH$ |
| 8-F | H | F | H | $CH_2C\equiv CH$ | 8-F | H | F | H | $CH(CH_3)C\equiv CH$ |
| 8-F | H | F | $CH_3$ | $CH_2C\equiv CH$ | 8-F | H | F | $CH_3$ | $CH(CH_3)C\equiv CH$ |
| 5-F | 5-F | F | H | $CH_2C\equiv CH$ | 5-F | 5-F | F | H | $CH(CH_3)C\equiv CH$ |
| 6-F | 6-F | F | H | $CH_2C\equiv CH$ | 6-F | 6-F | F | H | $CH(CH_3)C\equiv CH$ |
| 7-F | 7-F | F | H | $CH_2C\equiv CH$ | 7-F | 7-F | F | H | $CH(CH_3)C\equiv CH$ |
| 7-F | 7-F | F | $CH_3$ | $CH_2C\equiv CH$ | 7-F | 7-F | F | $CH_3$ | $CH(CH_3)C\equiv CH$ |
| 8-F | 8-F | F | H | $CH_2C\equiv CH$ | 8-F | 8-F | F | H | $CH(CH_3)C\equiv CH$ |
| 5-Cl | H | F | H | $CH_2C\equiv CH$ | 5-Cl | H | F | H | $CH(CH_3)C\equiv CH$ |
| 5-Cl | H | F | $CH_3$ | $CH_2C\equiv CH$ | 5-Cl | H | F | $CH_3$ | $CH(CH_3)C\equiv CH$ |
| 6-Cl | H | F | H | $CH_2C\equiv CH$ | 6-Cl | H | F | H | $CH(CH_3)C\equiv CH$ |
| 6-Cl | H | F | $CH_3$ | $CH_2C\equiv CH$ | 6-Cl | H | F | $CH_3$ | $CH(CH_3)C\equiv CH$ |
| 7-Cl | H | F | H | $CH_2C\equiv CH$ | 7-Cl | H | F | H | $CH(CH_3)C\equiv CH$ |
| 7-Cl | H | F | $CH_3$ | $CH_2C\equiv CH$ | 7-Cl | H | F | $CH_3$ | $CH(CH_3)C\equiv CH$ |
| 8-Cl | H | F | H | $CH_2C\equiv CH$ | 8-Cl | H | F | H | $CH(CH_3)C\equiv CH$ |
| 8-Cl | H | F | $CH_3$ | $CH_2C\equiv CH$ | 8-Cl | H | F | $CH_3$ | $CH(CH_3)C\equiv CH$ |
| 5-Cl | 5-Cl | F | H | $CH_2C\equiv CH$ | 5-Cl | 5-Cl | F | H | $CH(CH_3)C\equiv CH$ |
| 6-Cl | 6-Cl | F | H | $CH_2C\equiv CH$ | 6-Cl | 6-Cl | F | H | $CH(CH_3)C\equiv CH$ |
| 7-Cl | 7-Cl | F | H | $CH_2C\equiv CH$ | 7-Cl | 7-Cl | F | H | $CH(CH_3)C\equiv CH$ |
| 7-Cl | 7-Cl | F | $CH_3$ | $CH_2C\equiv CH$ | 7-Cl | 7-Cl | F | $CH_3$ | $CH(CH_3)C\equiv CH$ |
| 8-Cl | 8-Cl | F | H | $CH_2C\equiv CH$ | 8-Cl | 8-Cl | F | H | $CH(CH_3)C\equiv CH$ |

TABLE 4

| $R^3$ | $R^4$ | $R^3$ | $R^4$ | $R^3$ | $R^4$ | $R^3$ | $R^4$ |
|---|---|---|---|---|---|---|---|
| | Compounds of Formula Ik wherein Q = Q-1; $R^1$ = 6-F; $R^2$ = H; $R^5$ = Cl | | | | | | |
| Cl | H | Cl | $SCH_2C\equiv CH$ | Cl | $CH=CHCO_2$(i-Pr) | Cl | $OCH_2OCH_3$ |
| F | H | F | $SCH_2C\equiv CH$ | F | $CH=CHCO_2$(i-Pr) | F | $OCH_2OCH_3$ |
| Cl | O-(n-Pr) | Cl | $SCH(CH_3)C\equiv CH$ | Cl | $OCH_2CO_2$(i-Pr) | Cl | $SCH_2CO_2Et$ |
| F | O-(n-Pr) | F | $SCH(CH_3)C\equiv CH$ | F | $OCH_2CO_2$(i-Pr) | F | $SCH_2CO_2Et$ |
| Cl | $OCH_2CF_3$ | Cl | $NHSO_2CH_3$ | Cl | $OCH_2OPh$ | Cl | $OCH_2CO$(i-Pr) |
| Cl | $CO_2$(i-Pr) | F | $NHSO_2CH_3$ | F | $OCH_2OPh$ | F | $OCH_2CO$(i-Pr) |
| F | $CO_2$(i-Pr) | Cl | $OCH_2CO_2$(n-pentyl) | F | $OCH_2CO_2$(n-pentyl) | | |
| | Compounds of Formula II wherein Q = Q-1; $R^1$ = 6-F; $R^2$ = H; $R^5$ = Cl | | | | | | |
| Cl | H | Cl | $SCH_2C\equiv CH$ | Cl | $CH=CHCO_2$(i-Pr) | Cl | $OCH_2OCH_3$ |
| F | H | F | $SCH_2C\equiv CH$ | F | $CH=CHCO_2$(i-Pr) | F | $OCH_2OCH_3$ |
| Cl | O-(n-Pr) | Cl | $SCH(CH_3)C\equiv CH$ | Cl | $OCH_2CO_2$(i-Pr) | Cl | $SCH_2CO_2Et$ |
| F | O-(n-Pr) | F | $SCH(CH_3)C\equiv CH$ | F | $OCH_2CO_2$(i-Pr) | F | $SCH_2CO_2Et$ |
| Cl | $OCH_2CF_3$ | Cl | $NHSO_2CH_3$ | Cl | $OCH_2OPh$ | Cl | $OCH_2CO$(i-Pr) |
| Cl | $CO_2$(i-Pr) | F | $NHSO_2CH_3$ | F | $OCH_2OPh$ | F | $OCH_2CO$(i-Pr) |
| F | $CO_2$(i-Pr) | Cl | $OCH_2CO_2$(n-pentyl) | F | $OCH_2CO_2$(n-pentyl) | | |

TABLE 5

Compounds of Formula Ik wherein Q = Q-4; W = S;

| $R^1$ | $R^2$ | $R^3$ | $R^9$ | $R^1$ | $R^2$ | $R^3$ | $R^9$ | $R^1$ | $R^2$ | $R^3$ | $R^9$ |
|---|---|---|---|---|---|---|---|---|---|---|---|
| 5-F | H | F | $CH_2C\equiv CH$ | 5-Cl | H | F | $CH_2C\equiv CH$ | 6-F | 6-F | F | $CH_2C\equiv CH$ |
| 5-F | H | F | $CH_2C\equiv CH$ | 5-Cl | H | F | $CH_2C\equiv CH$ | 6-F | 6-F | F | $CH_2C\equiv CH$ |
| 6-F | H | F | $CH_2C\equiv CH$ | 6-Cl | H | F | $CH_2C\equiv CH$ | 7-F | 7-F | F | $CH_2C\equiv CH$ |
| 6-F | H | F | $CH_2C\equiv CH$ | 6-Cl | H | F | $CH_2C\equiv CH$ | 6-Cl | 6-Cl | F | $CH_2C\equiv CH$ |
| 7-F | H | F | $CH_2C\equiv CH$ | 7-Cl | H | F | $CH_2C\equiv CH$ | 6-Cl | 6-Cl | F | $CH_2C\equiv CH$ |
| 7-F | H | F | $CH_2C\equiv CH$ | 7-Cl | H | F | $CH_2C\equiv CH$ | 7-Cl | 7-Cl | F | $CH_2C\equiv CH$ |
| 5-F | 5-F | F | $CH_2C\equiv CH$ | 5-Cl | 5-Cl | F | $CH_2C\equiv CH$ | | | | |

| $R^1$ | $R^2$ | $R^3$ | $R^9$ | $R^1$ | $R^2$ | $R^3$ | $R^9$ |
|---|---|---|---|---|---|---|---|
| 5-F | H | F | $CH(CH_3)C\equiv CH$ | 5-Cl | H | F | $CH(CH_3)C\equiv CH$ |
| 5-F | H | F | $CH(CH_3)C\equiv CH$ | 5-Cl | H | F | $CH(CH_3)C\equiv CH$ |
| 6-F | H | F | $CH(CH_3)C\equiv CH$ | 6-Cl | H | F | $CH(CH_3)C\equiv CH$ |
| 6-F | H | F | $CH(CH_3)C\equiv CH$ | 6-Cl | H | F | $CH(CH_3)C\equiv CH$ |
| 7-F | H | F | $CH(CH_3)C\equiv CH$ | 7-Cl | H | F | $CH(CH_3)C\equiv CH$ |
| 7-F | H | F | $CH(CH_3)C\equiv CH$ | 7-Cl | H | F | $CH(CH_3)C\equiv CH$ |
| 5-F | 5-F | F | $CH(CH_3)C\equiv CH$ | 5-Cl | 5-Cl | F | $CH(CH_3)C\equiv CH$ |
| 6-F | 6-F | F | $CH(CH_3)C\equiv CH$ | 6-Cl | 6-Cl | F | $CH(CH_3)C\equiv CH$ |
| 6-F | 6-F | F | $CH(CH_3)C\equiv CH$ | 6-Cl | 6-Cl | F | $CH(CH_3)C\equiv CH$ |
| 7-F | 7-F | F | $CH(CH_3)C\equiv CH$ | 7-Cl | 7-Cl | F | $CH(CH_3)C\equiv CH$ |

Compounds of the Formula II wherein Q = Q-4; W = S;

| $R^1$ | $R^2$ | $R^3$ | $R^9$ | $R^1$ | $R^2$ | $R^3$ | $R^9$ | $R^1$ | $R^2$ | $R^3$ | $R^9$ |
|---|---|---|---|---|---|---|---|---|---|---|---|
| 5-F | H | F | $CH_2C\equiv CH$ | 5-Cl | H | F | $CH_2C\equiv CH$ | 7-F | 7-F | F | $CH_2C\equiv CH$ |
| 5-F | H | F | $CH_2C\equiv CH$ | 5-Cl | H | F | $CH_2C\equiv CH$ | 7-F | 7-F | F | $CH_2C\equiv CH$ |
| 6-F | H | F | $CH_2C\equiv CH$ | 6-Cl | H | F | $CH_2C\equiv CH$ | 8-F | 8-F | F | $CH_2C\equiv CH$ |
| 6-F | H | F | $CH_2C\equiv CH$ | 6-Cl | H | F | $CH_2C\equiv CH$ | 7-Cl | 7-Cl | F | $CH_2C\equiv CH$ |
| 7-F | H | F | $CH_2C\equiv CH$ | 7-Cl | H | F | $CH_2C\equiv CH$ | 7-Cl | 7-Cl | F | $CH_2C\equiv CH$ |
| 7-F | H | F | $CH_2C\equiv CH$ | 7-Cl | H | F | $CH_2C\equiv CH$ | 8-Cl | 8-C | F | $CH_2C\equiv CH$ |
| 8-F | H | F | $CH_2C\equiv CH$ | 8-Cl | H | F | $CH_2C\equiv CH$ | 6-F | 6-F | F | $CH_2C\equiv CH$ |
| 8-F | H | F | $CH_2C\equiv CH$ | 8-Cl | H | F | $CH_2C\equiv CH$ | 6-Cl | 6-Cl | F | $CH_2C\equiv CH$ |
| 5-F | 4-F | F | $CH_2C\equiv CH$ | 5-Cl | 5-Cl | F | $CH_2C\equiv CH$ | | | | |

| $R^1$ | $R^2$ | $R^3$ | $R^9$ | $R^1$ | $R^2$ | $R^3$ | $R^9$ |
|---|---|---|---|---|---|---|---|
| 5-F | H | F | $CH(CH_3)C\equiv CH$ | 5-Cl | H | F | $CH(CH_3)C\equiv CH$ |
| 5-F | H | F | $CH(CH_3)C\equiv CH$ | 5-Cl | H | F | $CH(CH_3)C\equiv CH$ |
| 6-F | H | F | $CH(CH_3)C\equiv CH$ | 6-Cl | H | F | $CH(CH_3)C\equiv CH$ |
| 6-F | H | F | $CH(CH_3)C\equiv CH$ | 6-Cl | H | F | $CH(CH_3)C\equiv CH$ |
| 7-F | H | F | $CH(CH_3)C\equiv CH$ | 7-Cl | H | F | $CH(CH_3)C\equiv CH$ |
| 7-F | H | F | $CH(CH_3)C\equiv CH$ | 7-Cl | H | F | $CH(CH_3)C\equiv CH$ |
| 8-F | H | F | $CH(CH_3)C\equiv CH$ | 8-Cl | H | F | $CH(CH_3)C\equiv CH$ |
| 8-F | H | F | $CH(CH_3)C\equiv CH$ | 8-Cl | H | F | $CH(CH_3)C\equiv CH$ |
| 5-F | 5-F | F | $CH(CH_3)C\equiv CH$ | 5-Cl | 5-Cl | F | $CH(CH_3)C\equiv CH$ |
| 6-F | 6-F | F | $CH(CH_3)C\equiv CH$ | 6-Cl | 6-Cl | F | $CH(CH_3)C\equiv CH$ |
| 7-F | 7-F | F | $CH(CH_3)C\equiv CH$ | 7-Cl | 7-Cl | F | $CH(CH_3)C\equiv CH$ |

TABLE 5-continued

| | | | | | | | |
|---|---|---|---|---|---|---|---|
| 7-F | 7-F | F | CH(CH₃)C=CH | 7-Cl | 7-Cl | F | CH(CH₃)C=CH |
| 8-F | 8-F | F | CH(CH₃)C=CH | 8-Cl | 8-Cl | F | CH(CH₃)C=CH |

TABLE 6

| $R^1$ | $R^2$ | $R^3$ | $R^1$ | $R^2$ | $R^3$ | $R^1$ | $R^2$ | $R^3$ | $R^1$ | $R^2$ | $R^3$ |
|---|---|---|---|---|---|---|---|---|---|---|---|
| Compounds of Formula Ik wherein Q = Q-5; $R^6 = R^7 = CF_3$; ||||||||||||
| 5-F | H | F | 6-F | 6-F | F | 7-Cl | H | F | 5-F | 5-F | F |
| 5-F | H | Cl | 6-F | 6-F | Cl | 7-Cl | H | Cl | 5-F | 5-F | Cl |
| 6-F | H | F | 7-F | 7-F | F | 5-Cl | 5-Cl | F | 6-Cl | H | F |
| 6-F | H | Cl | 7-F | 7-F | Cl | 5-Cl | 5-Cl | Cl | 6-Cl | H | Cl |
| 7-F | H | F | 5-Cl | H | F | 6-Cl | 6-Cl | F | 7-Cl | 7-Cl | F |
| 7-F | H | Cl | 5-Cl | H | Cl | 6-Cl | 6-Cl | Cl | 7-Cl | 7-Cl | Cl |
| Compounds of Formula II wherein Q = Q-5; $R^6 = R^7 = CF_3$; ||||||||||||
| 5-F | H | F | 5-F | 5-F | F | 5-Cl | 5-Cl | F | 6-F | 6-F | F |
| 5-F | H | Cl | 5-F | 5-F | Cl | 5-Cl | 5-Cl | Cl | 6-F | 6-F | Cl |
| 6-F | H | F | 7-F | 7-F | F | 8-Cl | H | F | 7-Cl | H | F |
| 6-F | H | Cl | 7-F | 7-F | Cl | 8-Cl | H | Cl | 7-Cl | H | Cl |
| 7-F | H | F | 7-F | 8-F | F | 6-Cl | 6-Cl | F | 8-CL | 8-Fl | F |
| 7-F | H | Cl | 8-F | 8-F | Cl | 6-Cl | 6-Cl | Cl | 8-Cl | 8-Cl | Cl |
| 8-F | H | F | 6-Cl | H | F | 7-Cl | 7-Cl | F | | | |
| 8-F | H | Cl | 6-Cl | H | Cl | 7-Cl | 7-Cl | Cl | | | |

Formulation/Utility

The compounds of this invention are useful as herbicides in agriculture. Typically, such compound(s) can be formulated in an effective amount with conventional additives including a carrier therefor (comprising a surfactant and/or a solid or liquid diluent) and applied by known methods to the locus to be protected.

Compounds of this invention will generally be used in formulation with an agriculturally suitable carrier comprising a liquid or solid diluent or an organic solvent. Useful formulations include dusts, granules, pellets, solutions, suspensions, emulsions, wettable powders, emulsifiable concentrates, dry flowables and the like, consistent with the physical properties of the active ingredient, mode of application and environmental factors such as soil type, moisture and temperature. Sprayable formulations can be extended in suitable media and used at spray volumes from about one to several hundred liters per hectare. High strength compositions are primarily used as intermediates for further formulation. The formulations will typically contain effective amounts of active ingredient, diluent and surfactant within the following approximate ranges which add up 100 weight percent.

| | Weight Percent | | |
|---|---|---|---|
| | Active Ingredient | Diluent | Surfactant |
| Wettable Powders | 25–90 | 0–74 | 1–10 |
| Oil Suspensions, Emulsions, Solutions, (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositrons | 90–99 | 0–10 | 0–2 |

Typical solid diluents are described in Watkins, et al., *Handbook of insecticide Dust Diluents and Carriers*, 2nd Ed., Dorland Books, Caldwell, N.J. Typical liquid diluents and solvents are described in Marsden, *Solvents Guide*, 2nd Ed., Interscience, New York, (1950). *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, (1964), list surfactants and recommended uses. All formulations can contain minor amounts of additives to reduce foam, caking, corrosion, microbiological growth, etc.

Solutions are prepared by simply mixing the ingredients. Fine solid compositions are made by blending and, usually, grinding as in a hammer mill or fluid energy mill. Water-dispersible granules can be produced by agglomerating a free powder composition; see for example, Cross et al., *Pesticide Formulations*, Washington, D.C., (1988), pp 251–259. Suspensions are prepared by wet-milling; see, for example, U.S. Pat. No. 3,060,084. Granules and pellets can be made by spraying the active material upon preformed granular carriers or by agglomeration techniques. See Browning, "Agglomeration", *Chemical Engineering*, Dec. 4, 1967, pp 147–48, *Perry's Chemical Engineer's Handbook*, 4th Ed., McGraw-Hill, New York, (1963), pp 8–57 and following, and WO 91/13546. Pellets can be prepared as described in U.S. Pat. No. 4,172,714. Water-dispersible and water-soluble granules can also be prepared as taught in DE 3,246,493.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science*, John Wiley and Sons, Inc., New York, (1961), pp 81–96; and Hance et al., *Weed Control Handbook*, 8th Ed., Blackwell Scientific Publications, Oxford, (1989).

In the following Examples, all percentages are by weight and all formulations are worked up in conventional ways. The compound number refers to the compound in Index Table A hereinafter.

| Example A | |
|---|---|
| High Strength Concentrate | |
| Compound 12 | 98.5% |
| silica aerogel | 0.5% |
| synthetic amorphous fine silica | 1.0%. |

| Example B | |
|---|---|
| Wettable Powder | |
| Compound 12 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

| Example C | |
|---|---|
| Granule | |
| Compound 12 | 10.0% |
| attapulgite granules (low volatile matter, 0.71/0.30 mm; U.S.S. No. 25–50 sieves) | 90.0%. |

Example D

Extruded Pellet

| | |
|---|---|
| Compound 12 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

The compounds of the present invention are highly active preemergent and/or postemergent herbicides and/or plant growth regulants. Many of them have utility for broad-spectrum pre- and/or postemergence weed control in areas where complete control of all vegetation is desired such as around fuel storage tanks, industrial storage areas, parking lots, drive-in theaters, around billboards and highway and railroad structures. Some of the compounds are useful for the control of selected grass and broadleaf weeds with tolerance to important agronomic crops which include but are not limited to barley, cotton, wheat, corn, soybeans, rice, citrus, peanut, and plantation crops such as sugarcane, coffee, banana, oil palm, rubber, grapes, fruit trees, nut trees, turf, pineapple and loblolly pine. The compounds of the instant invention are particularly useful on plantation crops such as sugarcane, coffee, banana, oil palm, rubber, grapes, fruit trees, nut trees, turf, pineapple and loblolly pine. Those skilled in the art will appreciate that not all compounds are equally effective against all weeds. Alternatively, the subject compounds are useful to modify plant growth.

Compounds of this invention can be used alone or in combination with other commercial herbicides, insecticides or fungicides. A mixture of one or more of the following herbicides with a compound of this invention can be particularly useful for weed control: acetochlor, acifluorfen, acrolein, 2-propenal, alachlor, ametryn, amidosulfuron, ammonium sulfamate, amitrole, anilofos, asulam, atrazine, barban, benefin, bensulfuron methyl, bensulide, bentazon, benzofluor, benzoylprop, bifenox, bromacil, bromoxynil, bromoxynil heptanoate, bromoxynil octanoate, butachlor, buthidazole, butralin, butylate, cacodylic acid, 2-chloro-N, N-di-2-propenyl-acetamide, 2-chloroallyl diethyldithiocarbamate, chloramben, chlorbromuron, chloridazon, chlorimuron ethyl, chlormethoxynil, chlornitrofen, chloroxuron, chlorpropham, chlorsulfuron, chlortoluron, cinmethylin, cinosulfuron, clethodim, clomazone, cloproxydim, clopyralid, calcium salt of methylarsonic acid, cyanazine, cycloate, cycluron, cyperquat, cyprazine, cyprazole, cypromid, dalapon, dazomet, dimethyl 2,3,5,6-tetrachloro-1,4-benzenedicarboxylate, desmedipham, desmetryn, dicamba, dichlobenil, dichlorprop, diclofop, diethatyl, difenzoquat, diflufenican, dimepiperate, dinitramine, dinoseb, diphenamid, dipropetryn, diquat, diuron, 2-methyl-4,6-dinitrophenol, disodium salt of methylarsonic acid, dymron, endothall, S-ethyl dipropylcarbamothioate, esprocarb, ethalfluralin, ethametsulfuron methyl, ethofumesate, fenac, fenoxaprop, fenuron, salt of fenuron and trichloroacetic acid, flamprop, fluazifop, fluazifop-P, fluchloralin, flumesulam, flumipropyn, fluomemron, fluorochloridone, fluorodifen, fluoroglycofen, flupoxam, fluridone, fluroxypyr, fluzasulfuron, fomesafen, fosamine, glyphosate, glyphosate salts, haloxyfop, hexaflurate, hexazinone, imazamethabenz, imazapyr, imazaquin, imazamethabenz methyl, imazethapyr, imazosulfuron, ioxynil, isopropalin, isoproturon, isouron, isoxaben, karbutilate, lactofen, lenacil, linuron, metobenzuron, metsulfuron methyl, methylarsonic acid, monoammonium salt of methylarsonic acid, (4-chloro-2-methylphenoxy)acetic acid, S,S'-dimethyl-2-(difluoromethyl)-4-(2-methylpropyl)-6-(trifluoromethyl)-3,5-pyridinedicarbothioate, mecoprop, mefenacet, mefluidide, methalpropalin, methabenzthiazuron, metham, methazole, methoxuron, metolachlor, metribuzin, 1,2-dihydropyridazine-3,6-dione, molinate, monolinuron, monuron, monuron salt and trichloroacetic acid, monosodium salt of methylarsonic acid, napropamide, naptalam, neburon, nicosulfuron, nitralin, nitrofen, nitrofluorfen, norea, norflurazon, oryzalin, oxadiazon, oxyfluorfen, paraquat, pebulate, pendimethalin, perfluidone, phenmedipham, picloram, 5-[2-chloro-4-(trifluoromethyl)phenoxy]-2-nitroacetophenone oxime-O-acetic acid methyl ester, pretilachlor, primisulfuron, procyazine, profluralin, prometon, prometryn, pronamide, propachlor, propanil, propazine, propham, prosulfalin, prynachlor, pyrazolate, pyrazon, pyrazosulfuron ethyl, quinchlorac, quizalofop ethyl, rimsulfuron, secbumeton, sethoxydim, siduron, simazine, 1-(α,α-dimethylbenzyl)-3-(4-methylphenyl)urea, sulfometuron methyl, trichloroacetic acid, tebuthiuron, terbacil, terbuchlor, terbuthylazine, terbutol, terbutryn, thifensulfuron methyl, thiobencarb, tri-allate, trialkoxydim, triasulfuron, tribenuron methyl, triclopyr, tridiphane, trifluralin, trimeturon, (2,4-dichlorophenoxy)acetic acid, 4-(2,4-dichlorophenoxy)butanoic acid, vernolate, and xylachlor.

In certain instances, combinations with other herbicides having a similar spectrum of control but a different mode of action will be particularly advantageous for resistance management.

A herbicidally effective amount of the compounds of this invention is determined by a number of factors. These factors include: formulation selected, method of application, amount and type of vegetation present, growing conditions, etc. In general, a herbicidally effective amount of a compound(s) of this invention is applied at rates from about 0.005 to 5.0 kg/ha with a preferred rate range of 0.010 to 2.0 kg/ha. One skilled in the art can easily determine application rates necessary for the desired level of weed control.

The following Tests demonstrate the control efficacy of the compounds of this invention against specific weeds. The weed control afforded by the compounds is not limited, however, to these species. See Index Tables A and B for compound descriptions.

Index Table A

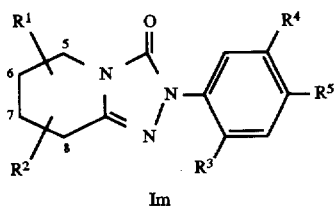

Im

Compound of Formula Im wherein:

| Cmpd No. | R¹ | R² | R³ | R⁴ | R⁵ | m.p. (°C.)[1,2] |
|---|---|---|---|---|---|---|
| 1 | 6-OH | H | Cl | OCH₂C≡CH | Cl | oil |
| 2 | 8-OH | H | Cl | OCH₂C≡CH | Cl | 168–170 |
| 3 | 8-Br | H | Cl | OC(O)Me | Cl | 75–83 |
| 4 | 8-Br | H | Cl | OC(O)Me | Cl | 77–82 |
| 5 | 8-Br | H | Cl | OS(O)₂(4-CH₃—Ph) | Cl | oil |
| 6 | 8-Br | 8-Br | Cl | OS(O)₂(4-CH₃—Ph) | Cl | 161–162 d |
| 7 | 6-Br | H | Cl | OCH₂C≡CH | Cl | oil |
| 8 | 6-F | H | Cl | OCH₂C≡CH | Cl | oil |
| 9 | 6-(=O) | | Cl | OCH₂C≡CH | Cl | oil |
| 10 | 6-OC(O)Me | H | Cl | OCH₂C≡CH | Cl | oil |
| 11 | 8-F | H | Cl | OCH₂C≡CH | Cl | oil |
| 12 | 8-Cl | H | Cl | OCH₂C≡CH | Cl | oil |
| 13 | 7-OH | 8-OH | Cl | OS(O)₂(4-CH₃—Ph) | Cl | glass |
| 14 | 8-OC(O)Me | H | Cl | OCH₂C≡CH | Cl | oil |
| 15 | 7-OH | 8-OH | Cl | OCH₂C≡CH | Cl | oil |
| 16 | 8-OH | H | Cl | OS(O)₂(4-CH₃—Ph) | Cl | oil |
| 17 | 8-(=O) | | Cl | OS(O)₂(4-CH₃—Ph) | Cl | oil |
| 18 | 8-(=O) | | Cl | OCH₂C≡CH | Cl | oil |
| 19 | 7-OH | H | Cl | OCH₂C≡CH | Cl | oil |
| 20 | 8-F | H | Cl | OCH₃ | Cl | 148–151 |
| 21 | 6-OH | H | H | H | F | oil |
| 22 | 6-Cl | H | Cl | OCH₂C≡CH | Cl | oil |
| 23 | 8-OH | H | Cl | OCH₃ | Cl | 245–247 |
| 24 | 6-OH | H | Cl | OCH₂C≡CH | Cl | 186–187 |
| 25 | 6-F | H | Cl | OCH₂C≡CH | Cl | oil |
| 26 | 6-Cl | H | Cl | OCH₂C≡CH | Cl | oil |
| 27 | 7-Cl | H | Cl | OCH₂C≡CH | Cl | oil |
| 28 | 7-F | H | Cl | OCH₂C≡CH | Cl | oil |
| 29 | 8-OH | H | Cl | OH | Cl | 238–240 d |
| 30 | 8-Br | H | Cl | OH | Cl | 187–190 |
| 31 | 7-OH | 8-OH | Cl | OH | Cl | 215–218 |
| 32 | 8-OH | H | Cl | OH | Cl | oil |
| 33 | 8-(=O) | | Cl | OH | Cl | oil |

Index Table B

Compound of Formula In wherein:

| Cmpd No. | R¹ | R³ | R⁴ | R⁵ | m.p. (°C.)[1] |
|---|---|---|---|---|---|
| 36 | H | Cl | OS(O)₂(4-CH₃—Ph) | Cl | oil |
| 37 | H | Cl | OH | Cl | oil |
| 38 | Br | Cl | OH | Cl | 246–247 |
| 39 | Br | Cl | OC(O)Me | Cl | oil |

Cmpd 34: R¹ = 5-F  oil[1]
Cmpd 35: R¹ = 7-Cl  oil[1]

Cmpd 40: mp 151–157° C.

[1] ¹H NMR data for oils and glass in Index Table C.
[2] d = decomposed

INDEX TABLE C

| Cmpd No. | ¹HNMR Data (solvent = CDCl₃ unless otherwise indicated, in ppm downfield from tetramethylsilane) |
|---|---|
| 1 | 7.55(s, 1H), 7.2(s, 1H), 4.8(s, 2H), 4.4(m, 1H), 3.75(m, 2H), 3.2 (s, 1H), 3.0(m, 1H), 2.75(m, 1H), 2.6(s, 1H), 2.1(m, 1H), 1.9 (m, 1H). |
| 5 | 7.78(d, 2H), 7.55(s, 1H), 7.50(s, 1H), 7.35(d, 2H), 5.27(t, 1H), 4.0(m, 1H), 3.61(m, 1H), 2.45(s, 3H), 2.1–2.5(m, 4H). |
| 7 | 7.6(s, 1H), 7.1(s, 1H), 4.8(q, 2H), 4.6(m, 1H), 4.0(m, 1H), 3.8 (m, 1H), 3.2(m, 1H), 3.0(m, 1H), 2.6(m, 1H), 2.4(m, 2H). |
| 8 | 7.55(s, 1H), 7.2(s, 1H), 5.4, 5.2(2m, 1H), 4.8(d, 2H), 4.1(m, 1H), 3.8–3.6(4d, 1H), 2.95(m, 2H), 2.6(m, 1H), 2.5(m, 1H), 2.0 (m, 1H). |
| 9 | 7.55(s, 1H), 7.2(s, 1H), 4.8(s, 2H), 4.4(s, 2H), 3.15(m, 2H), 2.8 (m, 2H), 2.6(s, 1H). |
| 10 | 7.55(s, 1H), 7.2(s, 1H), 5.4(m, 1H), 4.8(s, 2H), 3.95(m, 1H), 3.8 (dd, 1H), 2.9(m, 2H), 2.6(s, 1H), 2.3(m, 1H), 2.1(s, 3H), 2.0 (m, 1H). |
| 11 | 7.55(s, 1H), 7.2(s, 1H), 5.6, 5.5(2m, 1H), 4.8(s, 2H), 4.0(m, 1H), 3.55(m, 1H), 2.6(m, 1H), 2.5–1.8(m, 4H). |
| 12 | 7.55(s, 1H), 7.2(s, 1H), 5.15(t, 1H), 4.8(s, 2H), 3.95(m, 1H), 3.6(m, 1H), 2.6(m, 1H), 2.5–2.0(m, 4H). |
| 13 | 7.81(d, 2H), 7.63(s, 1H), 7.50(s, 1H), 7.35(d, 2H), 4.62(dd, 1H), 4.15(m, 1H), 3.89(m, 1H), 3.71(m, 1H), 3.55(d, 1H), 2.77(d, 1H), 2.46(s, 3H), 2.36(m, 1H), 2.1(m, 1H). |
| 14 | 7.55(s, 1H), 7.15(m, 1H), 5.95(m, 1H), 4.8(s, 2H), 3.85(m, 1H), 3.6(m, 1H), 2.6(s, 1H), 2.2–2.0(m, 4H), 2.15(s, 3H). |
| 15 | (solvent = (CD₃)₂SO) 7.85(s, 1H), 7.35(s, 1H), 6.13(d, 1H), 5.44(d, 1H), 4.97(d, 2H), 4.35(m, 1H), 3.95(m, 1H), 3.70(t, 1H), 3.65(m, 1H), 3.5(m, 1H), 2.15(m, 1H), 1.9(m, 1H). |
| 16 | 7.78(d, 2H), 7.60(s, 1H), 7.50(s, 1H), 7.34(d, 2H), 4.85(m, 1H), 2.78(d, 1H), 2.45(s, 3H), 2.25(m, 1H), 2.0(m, 3H). |
| 17 | 7.77(d, 2H), 7.60(s, 1H), 7.53(s, 1H), 7.30(d, 2H), 4.00(m, 2H), 2.86(m, 2H), 2.46(s, 3H), 2.42(m, 2H). |
| 18 | (solvent = (CD₃)₂SO) 7.92(s, 1H), 7.42(s, 1H), 4.98(d, 2H), 3.8(t, 2H), 3.70(t, 1H), 2.75(t, 2H), 2.25(m, 2H). |
| 19 | 7.54(s, 1H), 7.16(s, 1H), 4.77(d, 2H), 4.40(m, 1H), 3.75–3.90 (m, 2H), 3.6(t, 1H), 2.9–3.0(m, 2H), 2.6(m, 1H), 2.0–2.2(m, 2H). |
| 21 | 7.9(m, 2H), 7.1(m, 2H), 4.5(m, 1H), 3.8(m, 2H), 3.0(m, 1H), 2.8(m, 1H), 2.2(m, 1H), 1.9(m, 1H), 1.6(br s, 1H). |
| 22 | 7.55(s, 1H), 7.2(s, 1H), 4.8(s, 2H), 4.6(m, 1H), 4.0(m, 2H), 3.15 (m, 1H), 2.9(m, 1H), 2.6(m, 1H), 2.3(m, 2H). |
| 25 | 7.55(s, 1H), 7.2(s, 1H), 6.3, 6.15(2t, 1H), 4.8(d, 2H), 3.0(m, 1H), 2.7(m, 1H), 2.6(m, 1H), 2.5(m, 1H), 2.2–1.8(m, 3H). |
| 26 | 7.55(s, 1H), 7.2(s, 1H), 6.2(m, 1H), 4.8(t, 2H), 3.0(m, 1H), 2.8 (m, 1H), 2.6(m, 1H), 2.6–2.0(m, 4H) |
| 27 | 7.55(s, 1H), 7.2(s, 1H), 4.8(d, 2H), 4.6(m, 1H), 4.0–3.8(m, 2H), 3.2(m, 2H), 2.65(m, 1H), 2.6(m, 1H), 2.4(m, 1H). |
| 28 | 7.6(s, 1H), 7.2(s, 1H), 5.4, 5.2(2q, 1H), 4.8(d, 2H), 4.0–3.75 (m, 2H), 3.3–2.8(m, 2H), 2.6(m, 1H), 2.5(m, 1H), 2.2–2.0(m, 1H). |
| 32 | (solvent = (CD₃)₂SO) 10.9(s, 1H), 7.65(s, 1H), 7.02(s, 1H), 5.22 (d, 1H), 4.17(m, 1H), 3.55(m, 2H), 2.80(m, 1H), 2.59(dd, 1H), 1.95(m, 2H). |
| 33 | (solvent = (CD₃)₂SO) 11.1(s, 1H), 7.75(s, 1H), 7.09(s, 1H), 3.78 (t, 2H), 2.74(d, 2H), 2.25(m, 2H). |
| 34 | 7.55(s, 1H), 7.2(s, 1H), 6.4, 6.2(2d, 1H), 4.8(s, 2H), 3.2–2.6(m, 4H), 2.6(s, 1H). |
| 35 | 7.55(s, 1H), 7.2(s, 1H), 5.2(d, 1H), 4.8(d, 2H), 4.0(m, 2H), 2.8 (m, 2H), 2.6(m, 1H). |
| 36 | 7.80(d, 2H), 7.62(s, 1H), 7.48(s, 1H), 7.34(d, 2H), 6.43(m, 2H), 3.89(t, 2H), 2.69(dt, 2H), 2.45(s, 3H). |
| 37 | 7.46(s, 1H), 7.10(s, 1H), 6.4(m, 2H), 3.89(t, 2H), 2.65(m, 2H). |
| 39 | 7.6(s, 1H), 7.35(s, 1H), 6.7(t, 1H), 3.9(t, 2H), 2.7(q, 2H), 2.35 (s, 3H). |

TEST A

Seeds of barley (*Hordeum vulgare*), barnyardgrass (*Echinochloa crus-galli*), bedstraw (*Gatlum aparine*), blackgrass (*Alopecurus myosuroides*), cheatgrass (*Bromus secalinus*), chickweed (*Stellaria media*), cocklebur (*Xanthium pensylvanicum*), corn (*Zea mays*), cotton (*Gossypium hirsutum*), crabgrass (*Digitaria spp.*), downy brome (*Bromus rectorum*), giant foxtail (*Setaria faberii*), lambsquarters (*Chenopodium album*), morningglory (*Ipomoea hederacea*), rape (*Brassica napus*), rice (*Oryza sativa*), sorghum (*Sorghum bicolor*), soybean (*Glycine max*), sugar beet (*Beta vulgaris*), velvetleaf (*Abutilon theophrasti*), wheat (*Triticum aestivum*), wild buckwheat (*Polygonum convolvulus*), wild oat (*Avena fatua*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from two to eighteen cm (one to four leaf stage) for postemergence treatments. Treated plants and controls were maintained in a greenhouse for twelve to sixteen days, after which all species were compared to controls and visually evaluated. Plant response ratings, summarized in Table A, are based on a scale of 0 to 10 where 0 is no effect and 10 is complete control. A dash (-) response means no test result.

TABLE A

| Rate 400 g/ha | \multicolumn{11}{c}{COMPOUND} |
| --- | --- | --- | --- | --- | --- | --- | --- | --- | --- | --- | --- |
|  | 8 | 10 | 11 | 12 | 14 | 20 | 21 | 22 | 23 | 35 | 36 | 38 |

POSTEMERGENCE

| | 8 | 10 | 11 | 12 | 14 | 20 | 21 | 22 | 23 | 35 | 36 | 38 |
| --- | --- | --- | --- | --- | --- | --- | --- | --- | --- | --- | --- | --- |
| Barley | 9 | 6 | 7 | 8 | 8 | 9 | 0 | 6 | 2 | 4 | 4 | 2 |
| Barnyardgrass | 10 | 3 | 10 | 10 | 10 | 10 | 0 | 10 | 5 | 9 | 3 | 2 |
| Bedstraw | 10 | 5 | 10 | 9 | 8 | 9 | 2 | 10 | 2 | 9 | 1 | 1 |
| Blackgrass | 10 | 4 | 10 | 9 | 9 | 10 | 0 | 10 | 2 | 9 | 3 | 2 |
| Chickweed | 10 | 4 | 10 | 2 | 4 | 3 | 0 | 9 | 0 | 5 | 1 | 2 |
| Cocklebur | 9 | 7 | 9 | 8 | 8 | 8 | 0 | 10 | 4 | 7 | 4 | 2 |
| Corn | 9 | 5 | 8 | 8 | 9 | 9 | 0 | 7 | 3 | 5 | 3 | 2 |
| Cotton | 10 | 10 | 10 | 10 | 10 | 10 | 0 | 10 | 9 | 10 | 9 | 9 |
| Crabgrass | 10 | 4 | 9 | 8 | 8 | 10 | 0 | 9 | 3 | 8 | 4 | 2 |
| Downy brome | 9 | 4 | 8 | 6 | 5 | 9 | 0 | 8 | 1 | 5 | 2 | 1 |
| Giant foxtail | 10 | 3 | 9 | 9 | 9 | 9 | 0 | 9 | 3 | 8 | 3 | 2 |
| Lambsquarter | 10 | 7 | 10 | 10 | 10 | 10 | 0 | 10 | 9 | 10 | 6 | 4 |
| Morningglory | 10 | 9 | 10 | 10 | 10 | 10 | 0 | 10 | 7 | 9 | 4 | 2 |
| Nutsedge | 10 | 8 | — | 5 | 6 | 10 | 0 | 6 | 1 | 5 | 0 | 1 |
| Rape | 10 | 6 | 10 | 10 | 9 | 9 | 0 | 10 | 7 | 8 | 5 | 1 |
| Rice | 10 | 5 | 9 | 8 | 8 | 9 | 0 | 9 | 5 | 6 | 3 | 3 |
| Sorghum | 10 | 4 | 9 | 9 | 9 | 9 | 0 | 9 | 3 | 6 | 3 | 3 |
| Soybean | 9 | 7 | 9 | 9 | 9 | 9 | 1 | 9 | 5 | 9 | 5 | 3 |
| Sugar beet | 10 | 7 | 10 | 10 | 10 | 10 | 0 | 10 | 7 | 10 | 6 | 3 |
| Velvetleaf | 10 | 10 | 10 | 10 | 10 | 10 | 0 | 10 | 9 | 10 | 8 | 2 |
| Wheat | 9 | 6 | 9 | 9 | 8 | 9 | 0 | 6 | 2 | 5 | 4 | 1 |
| Wild buckwheat | 10 | 10 | 10 | 10 | 10 | 10 | 2 | 10 | 9 | 10 | 3 | 2 |
| Wild oat | 10 | 5 | 9 | 8 | 9 | 9 | 0 | 9 | 1 | 8 | 3 | 2 |

PREMERGENCE

| | 8 | 10 | 11 | 12 | 14 | 20 | 21 | 22 | 23 | 35 | 36 | 38 |
| --- | --- | --- | --- | --- | --- | --- | --- | --- | --- | --- | --- | --- |
| Barley | 6 | 0 | 8 | 8 | 7 | 8 | 0 | 2 | 2 | 0 | 0 | 0 |
| Barnyardgrass | 10 | 7 | 10 | 9 | 10 | 10 | 0 | 9 | 7 | 4 | 0 | 0 |
| Bedstraw | 10 | 3 | 10 | 7 | 9 | 7 | 0 | 10 | 3 | 9 | 2 | 0 |
| Blackgrass | 8 | 1 | 10 | 9 | 9 | 10 | 0 | 9 | 2 | 6 | 0 | 0 |
| Chickweed | 10 | 2 | 10 | 4 | 8 | 4 | 0 | 10 | 0 | 2 | 0 | 0 |
| Cocklebur | 10 | 0 | 10 | 5 | 9 | 10 | 0 | 7 | 3 | 2 | 0 | 2 |
| Corn | 8 | 3 | 7 | 5 | 10 | 7 | 0 | 9 | 2 | 3 | 0 | 0 |
| Cotton | 9 | 0 | 10 | 7 | 9 | 8 | 0 | 9 | 3 | 1 | 0 | 0 |
| Crabgrass | 10 | 1 | 10 | 10 | 10 | 10 | 0 | 10 | 4 | 10 | 0 | 2 |
| Downy brome | 10 | 0 | 9 | 7 | 10 | 10 | 0 | 8 | 3 | 5 | 1 | 0 |
| Giant foxtail | 10 | 4 | 10 | 9 | 10 | 10 | 0 | 9 | 8 | 10 | 0 | 0 |
| Lambsquarter | 10 | 8 | 10 | 10 | 10 | 10 | 3 | 10 | 10 | 10 | 4 | 0 |
| Morningglory | 10 | 1 | 10 | 10 | 10 | 7 | 0 | 10 | 5 | 10 | 0 | 5 |
| Nutsedge | 3 | 2 | 3 | 1 | 8 | 4 | 0 | 2 | 8 | 1 | 3 | 0 |
| Rape | 10 | 2 | 10 | 10 | 10 | 10 | 0 | 10 | 8 | 8 | 1 | 0 |
| Rice | 9 | 5 | 9 | 5 | 8 | 9 | 0 | 5 | 3 | 2 | 0 | 0 |
| Sorghum | 10 | 2 | 10 | 10 | 9 | 10 | 0 | 7 | 2 | 4 | 0 | 0 |
| Soybean | 9 | 2 | 10 | 7 | 9 | 9 | 0 | 10 | 4 | 1 | 0 | 3 |
| Sugar beet | 10 | 4 | 10 | 10 | 10 | 10 | 0 | 10 | 9 | 10 | 3 | 0 |
| Velvetleaf | 10 | 10 | 10 | 10 | 10 | 10 | 0 | 10 | 9 | 10 | 0 | 0 |
| Wheat | 7 | 0 | 10 | 9 | 9 | 9 | 0 | 4 | 6 | 1 | 0 | 0 |
| Wild buckwheat | 10 | 2 | 10 | 10 | 10 | 10 | 0 | 10 | 8 | 10 | 0 | 0 |
| Wild oat | 9 | 0 | 10 | 10 | 9 | 10 | 0 | 9 | 6 | 6 | 0 | 0 |

| Rate 200 g/ha | \multicolumn{3}{c}{COMPOUND} |
| --- | --- | --- | --- |
|  | 6 | 24 | 40 |

POSTEMERGENCE

| | 6 | 24 | 40 |
| --- | --- | --- | --- |
| Barley | 2 | 3 | 0 |
| Barnyardgrass | 2 | 3 | 1 |
| Bedstraw | 1 | 3 | 2 |
| Blackgrass | 2 | 4 | 3 |
| Chickweed | 1 | 2 | 0 |
| Cocklebur | 2 | 3 | 2 |
| Corn | 2 | 2 | 1 |
| Cotton | 9 | 9 | 2 |
| Crabgrass | 5 | 4 | 1 |
| Downy brome | 2 | 3 | 0 |
| Giant foxtail | 3 | 3 | 2 |
| Lambsquarter | 4 | 4 | 3 |
| Morningglory | 3 | 5 | 1 |
| Nutsedge | 1 | 1 | — |
| Rape | 3 | 3 | 0 |
| Rice | 3 | 3 | 1 |
| Sorghum | 3 | 4 | 1 |
| Soybean | 3 | 2 | 3 |
| Sugar beet | 5 | 8 | 0 |
| Velvetleaf | 6 | 7 | 4 |
| Wheat | 5 | 4 | 0 |
| Wild buckwheat | 4 | 3 | 3 |
| Wild oat | 3 | 3 | 2 |

PREEMERGENCE

| | 6 | 24 | 40 |
| --- | --- | --- | --- |
| Barley | 1 | 0 | 0 |
| Barnyardgrass | 0 | 0 | 0 |
| Bedstraw | 2 | 0 | 0 |
| Blackgrass | 1 | 0 | 2 |
| Chickweed | 0 | 0 | 0 |
| Cocklebur | 0 | 0 | 0 |
| Corn | 0 | 0 | 0 |
| Cotton | 0 | 0 | 0 |
| Crabgrass | 3 | 0 | 0 |
| Downy brome | 1 | 0 | 2 |
| Giant foxtail | 0 | 0 | 0 |
| Lambsquarter | 0 | 0 | 0 |
| Morningglory | 0 | 0 | 0 |
| Nutsedge | 0 | 0 | 0 |
| Rape | 1 | 0 | 0 |
| Rice | 0 | 0 | 0 |
| Sorghum | 0 | 0 | 0 |
| Soybean | 0 | 0 | 0 |
| Sugar beet | 0 | 0 | 0 |
| Velvetleaf | 3 | 0 | 0 |
| Wheat | 0 | 0 | 0 |
| Wild buckwheat | 2 | 0 | 0 |
| Wild oat | 0 | 0 | 0 |

| Rate 50 g/ha | \multicolumn{4}{c}{COMPOUND} |
| --- | --- | --- | --- | --- |
|  | 6 | 24 | 37 | 40 |

POSTEMERGENCE

| | 6 | 24 | 37 | 40 |
| --- | --- | --- | --- | --- |
| Barley | 1 | 3 | 1 | 0 |
| Barnyardgrass | 2 | 3 | 2 | 1 |
| Bedstraw | 1 | 3 | 0 | 2 |
| Blackgrass | 1 | 3 | 2 | 2 |
| Chickweed | 1 | 0 | 0 | 0 |
| Cocklebur | 1 | 2 | 0 | 2 |
| Corn | 2 | 2 | 1 | 1 |
| Cotton | 5 | 9 | 4 | 2 |
| Crabgrass | 3 | 4 | 2 | 1 |
| Downy brome | 0 | 2 | 0 | 0 |
| Giant foxtail | 2 | 2 | 2 | 1 |
| Lambsquarter | 2 | 3 | 0 | 3 |
| Morningglory | 2 | 2 | 0 | 1 |
| Nutsedge | 1 | 0 | 0 | — |
| Rape | 2 | 0 | 0 | 0 |
| Rice | 2 | 3 | 0 | 1 |
| Sorghum | 2 | 3 | 2 | 1 |
| Soybean | 3 | 2 | 1 | 2 |
| Sugar beet | 4 | 7 | 2 | 0 |
| Velvetleaf | — | 7 | 0 | 3 |
| Wheat | 4 | 3 | 2 | 0 |
| Wild buckwheat | 3 | 2 | 0 | 1 |
| Wild oat | 3 | 3 | 2 | 2 |

PREEMERGENCE

| | 6 | 24 | 37 | 40 |
| --- | --- | --- | --- | --- |
| Barley | 1 | 0 | 0 | 0 |
| Barnyardgrass | 0 | 0 | 0 | 0 |
| Bedstraw | 0 | 0 | 0 | 0 |
| Blackgrass | 1 | 0 | 0 | 0 |
| Chickweed | 0 | 0 | 0 | 0 |
| Cocklebur | 0 | 0 | 0 | 0 |
| Corn | 0 | 0 | 2 | 0 |
| Cotton | 0 | 0 | 0 | 0 |
| Crabgrass | 0 | 0 | 3 | 0 |
| Downy brome | 0 | 0 | 0 | 0 |
| Giant foxtail | 0 | 0 | 2 | 0 |
| Lambsquarter | 0 | 0 | 0 | 0 |
| Morningglory | 0 | 0 | 0 | 0 |
| Nutsedge | 0 | 0 | 0 | 0 |
| Rape | 1 | 0 | 2 | 0 |

TABLE A-continued

| Rate | | | | | |
|---|---|---|---|---|---|
| Rice | 0 | 0 | 0 | 0 | |
| Sorghum | 0 | 0 | 0 | 0 | |
| Soybean | 0 | 0 | 0 | 0 | |
| Sugar beet | 0 | 0 | 0 | 0 | |
| Velvetleaf | 0 | 0 | 0 | 0 | |
| Wheat | 0 | 0 | 0 | 0 | |
| Wild buckwheat | 0 | 0 | 0 | 0 | |
| Wild oat | 0 | 0 | 0 | 0 | |

| Rate 100 g/ha | COMPOUND | | | | | | | | | | | | |
|---|---|---|---|---|---|---|---|---|---|---|---|---|---|
| | 8 | 9 | 10 | 11 | 12 | 14 | 20 | 21 | 22 | 23 | 35 | 36 | 38 |
| Barley | 7 | 4 | 3 | 7 | 5 | 5 | 7 | 0 | 4 | 1 | 4 | 3 | 1 |
| Barnyardgrass | 9 | 2 | 2 | 9 | 9 | 9 | 9 | 0 | 9 | 3 | 9 | 3 | 1 |
| Bedstraw | 9 | 7 | 4 | 10 | 9 | 6 | 9 | 0 | 9 | 2 | 6 | 1 | 1 |
| Blackgrass | 9 | 4 | 4 | 9 | 8 | 4 | 7 | 0 | 5 | 1 | 4 | 2 | 1 |
| Chickweed | 9 | 5 | 4 | 7 | 1 | 3 | 3 | 0 | 6 | 0 | 4 | 1 | 1 |
| Cocklebur | 9 | 4 | 6 | 10 | 7 | 7 | 7 | 0 | 7 | 3 | 7 | 3 | 1 |
| Corn | 8 | 2 | 2 | 7 | 5 | 5 | 5 | 0 | 6 | 3 | 2 | 3 | 1 |
| Cotton | 10 | 9 | 9 | 10 | 10 | 10 | 10 | 0 | 10 | 9 | 9 | 9 | 6 |
| Crabgrass | 7 | 3 | 3 | 8 | 8 | 3 | 6 | 0 | 8 | 3 | 4 | 3 | 2 |
| Downy brome | 7 | 3 | 3 | 8 | 5 | 3 | 7 | 0 | 3 | 1 | 4 | 2 | |
| Giant foxtail | 6 | 3 | 3 | 9 | 8 | 5 | 7 | 0 | 9 | 3 | 6 | 3 | 1 |
| Lambsquarter | 10 | 4 | 6 | 10 | 10 | 10 | 9 | 0 | 10 | 8 | 10 | 4 | 2 |
| Morningglory | 9 | 7 | 9 | 10 | 10 | 9 | 10 | 0 | 9 | 7 | 8 | 4 | 2 |
| Nutsedge | 10 | 1 | 4 | 4 | 3 | 2 | 2 | 0 | 3 | 1 | 2 | 0 | 1 |
| Rape | 9 | 4 | 6 | 9 | 9 | 8 | 8 | 0 | 10 | 5 | 7 | 3 | 1 |
| Rice | 8 | 5 | 4 | 9 | 7 | 5 | 7 | 0 | 9 | 3 | 4 | 3 | 2 |
| Sorghum | 9 | 4 | 3 | 8 | 7 | 8 | 9 | 0 | 9 | 3 | 4 | 3 | 3 |
| Soybean | 9 | 6 | 6 | 8 | 8 | 9 | 8 | 0 | 9 | 4 | 5 | 3 | 2 |
| Sugar beet | 10 | 7 | 7 | 10 | 8 | 10 | 10 | 0 | 9 | 6 | 8 | 4 | 2 |
| Velvetleaf | 10 | 7 | 7 | 10 | 9 | 9 | 10 | 0 | 10 | 5 | 8 | 5 | 1 |
| Wheat | 9 | 5 | 3 | 9 | 7 | 7 | 8 | 0 | 6 | 1 | 5 | 4 | 1 |
| Wild buckwheat | 10 | 8 | 7 | 10 | 10 | 10 | 9 | 0 | 10 | 7 | 9 | 2 | 2 |
| Wild oat | 8 | 3 | 3 | 8 | 4 | 6 | 8 | 0 | 8 | 0 | 5 | 2 | 1 |
| PREEMERGENCE | | | | | | | | | | | | | |
| Barley | 6 | 1 | 0 | 6 | 2 | 4 | 4 | 0 | 1 | 0 | 0 | 0 | 0 |
| Barnyardgrass | 9 | 0 | 1 | 10 | 8 | 9 | 10 | 0 | 8 | 2 | 1 | 0 | 0 |
| Bedstraw | 9 | 1 | 2 | 10 | 10 | 0 | 3 | 0 | 8 | 0 | 1 | 0 | 0 |
| Blackgrass | 7 | 2 | 1 | 9 | 7 | 5 | 9 | 0 | 8 | 0 | 3 | 1 | 0 |
| Chickweed | 10 | 0 | 0 | 9 | 2 | 0 | 2 | 0 | 10 | 0 | 3 | 0 | 0 |
| Cocklebur | 3 | 0 | 0 | 6 | 2 | 4 | 5 | 0 | 5 | 2 | 0 | 0 | 1 |
| Corn | 7 | 0 | 0 | 6 | 4 | 6 | 3 | 0 | 5 | 0 | 1 | 0 | 0 |
| Cotton | 10 | 0 | — | 7 | 0 | 2 | 1 | 0 | 2 | 0 | 0 | 0 | 0 |
| Crabgrass | 10 | 0 | — | 10 | 8 | 9 | 10 | 0 | 10 | 2 | 6 | 0 | 0 |
| Downy brome | 6 | 2 | 0 | 6 | 7 | 5 | 8 | 0 | 6 | 1 | 3 | 0 | 0 |
| Giant foxtail | 9 | 0 | 0 | 10 | 8 | 9 | 10 | 0 | 9 | 8 | 6 | 0 | 0 |
| Lambsquarter | 10 | 6 | 4 | 10 | 10 | 10 | 10 | 0 | 10 | 9 | 10 | 2 | 0 |
| Morningglory | 10 | 0 | 0 | 8 | 3 | 6 | 6 | 0 | 10 | 4 | 10 | 0 | 0 |
| Nutsedge | 1 | — | 0 | 2 | 0 | 1 | 2 | 0 | 1 | 0 | 0 | 0 | 0 |
| Rape | 8 | 1 | 2 | 10 | 5 | 8 | 9 | 0 | 9 | 3 | 2 | 1 | 0 |
| Rice | 7 | 0 | 2 | 8 | 4 | 6 | 7 | 0 | 3 | 2 | 0 | 0 | 0 |
| Sorghum | 9 | 0 | 0 | 4 | 3 | 7 | 5 | 0 | 3 | 0 | 0 | 0 | 0 |
| Soybean | 10 | 0 | 2 | 8 | 4 | 9 | 6 | 0 | 9 | 2 | 0 | 0 | 1 |
| Sugar beet | 10 | 6 | 2 | 10 | 10 | 10 | 10 | 0 | 10 | 7 | 10 | 2 | 0 |
| Velvetleaf | 10 | 4 | 5 | 10 | 9 | 10 | 10 | 0 | 10 | 9 | 9 | 0 | 0 |
| Wheat | 7 | 1 | 0 | 7 | 1 | 7 | 5 | 0 | 2 | 1 | 2 | 0 | 0 |
| Wild buckwheat | 10 | 1 | 0 | 10 | 8 | 10 | 9 | 0 | 6 | 3 | 7 | 0 | 0 |
| Wild oat | 8 | 0 | 0 | 9 | 5 | 7 | 7 | 0 | 9 | 2 | 3 | 0 | 0 |

| Rate 20 g/ha | COMPOUND 9 |
|---|---|
| POSTEMERGENCE | |
| Barley | 3 |
| Barnyardgrass | 2 |
| Bedstraw | 5 |
| Blackgrass | 1 |
| Chickweed | 3 |
| Cocklebur | 4 |
| Corn | 2 |
| Cotton | 7 |
| Crabgrass | 4 |
| Downy brome | 1 |
| Giant foxtail | 4 |
| Lambsquarter | 4 |
| Morningglory | 6 |
| Nutsedge | — |
| Rape | 3 |
| Rice | 4 |
| Sorghum | 3 |
| Soybean | 5 |
| Sugar beet | 4 |
| Velvetleaf | 5 |
| Wheat | 4 |
| Wild buckwheat | 7 |
| Wild oat | 3 |
| PREEMERGENCE | |
| Barley | 0 |
| Barnyardgrass | 0 |
| Bedstraw | 1 |
| Blackgrass | 0 |
| Chickweed | 0 |
| Cocklebur | 0 |
| Corn | 0 |
| Cotton | 0 |
| Crabgrass | 0 |
| Downy brome | 0 |
| Giant foxtail | 0 |
| Lambsquarter | 0 |
| Morningglory | 0 |
| Nutsedge | 0 |
| Rape | 1 |
| Rice | 0 |
| Sorghum | 0 |
| Soybean | 0 |
| Sugar beet | 2 |
| Velvetleaf | 3 |
| Wheat | 0 |
| Wild buckwheat | 1 |
| Wild oat | 0 |

| Rate 10 g/ha | COMPOUND 37 |
|---|---|
| POSTEMERGENCE | |
| Barley | 0 |
| Barnyardgrass | 0 |
| Bedstraw | 0 |
| Blackgrass | 0 |
| Chickweed | 0 |
| Cocklebur | 0 |
| Corn | 0 |
| Cotton | 0 |
| Crabgrass | 1 |
| Downy brome | 0 |
| Giant foxtail | — |
| Lambsquarter | 0 |
| Morningglory | — |
| Nutsedge | 0 |
| Rape | 0 |
| Rice | 0 |
| Sorghum | 0 |
| Soybean | 0 |
| Sugar beet | 0 |
| Velvetleaf | 0 |

TABLE A-continued

| | |
|---|---|
| Wheat | 1 |
| Wild buckwheat | 0 |
| Wild oat | 1 |
| PREEMERGENCE | |
| Barley | 0 |
| Barnyardgrass | 0 |
| Bedstraw | 0 |
| Blackgrass | 0 |
| Chickweed | 0 |
| Cocklebur | 0 |
| Corn | 0 |
| Cotton | 0 |
| Crabgrass | 0 |
| Downy brome | 0 |
| Giant foxtail | 0 |
| Lambsquarter | 0 |
| Morningglory | 0 |
| Nutsedge | 0 |
| Rape | 0 |
| Rice | 0 |
| Sorghum | 0 |
| Soybean | 0 |
| Sugar beet | 0 |
| Velvetleaf | 0 |
| Wheat | 0 |
| Wild buckwheat | 0 |
| Wild oat | 0 |

TEST B

Seeds of barnyardgrass (*Echinochloa crus-galli*), cheatgrass (*Bromus secalinus*), cocklebur (*Xanthium pensylvanicum*), crabgrass (*Digitaria spp.*), giant foxtail (*Setaria faberii*), morningglory (*Ipomoea spp.*), sorghum (*Sorghum bicolor*), velvetleaf (*Abutilon theophrasti*), and wild oat (*Avena fatua*) were planted into a sandy loam soil and treated preemergence, or with a soil drench(PDRN), with test chemicals dissolved in a non-phytotoxic solvent. At the same time, these crop and weed species were also treated postemergence, or sprayed to runoff(STRO), with test chemicals. Plants ranged in height from two to eighteen cm and were in the two to three leaf stage for the postemergence treatment. Treated plants and untreated controls were maintained in a greenhouse for approximately eleven days, after which all treated plants were compared to untreated controls and visually evaluated for injury. Plant response ratings, summarized in Table B, are based on a 0 to 10 scale where 0 is no effect and 10 is complete control. A dash (-) response means no test results.

TABLE B

| Rate 2000 g/ha | COMPOUND 7 |
|---|---|
| PDRN | |
| Barnyardgrass | 0 |
| Cocklebur | 0 |
| Crabgrass | 0 |
| Downy brome | 0 |
| Giant foxtail | 0 |
| Morningglory | 0 |
| Sorghum | 0 |
| Velvetleaf | 0 |
| Wild oats | 0 |
| STRO | |
| Barnyardgrass | 1 |
| Cocklebur | 0 |

TABLE B-continued

| | |
|---|---|
| Crabgrass | 1 |
| Downy brome | 1 |
| Giant foxtail | 2 |
| Morningglory | 1 |
| Sorghum | 1 |
| Velvetleaf | 5 |
| Wild oats | 2 |

| Rate 800 g/ha | COMPOUND | | | |
|---|---|---|---|---|
| | 3 | 4 | 13 | 30 |
| PREEMERGENCE | | | | |
| Barnyardgrass | 0 | 0 | 0 | 0 |
| Cocklebur | 0 | 0 | 0 | 0 |
| Crabgrass | 0 | 0 | 0 | 0 |
| Downy brome | 0 | 0 | 0 | 0 |
| Giant foxtail | 0 | 0 | 0 | 0 |
| Morningglory | 0 | 0 | 0 | 0 |
| Sorghum | 0 | 0 | 0 | 0 |
| Velvetleaf | 0 | 0 | 0 | 0 |
| Wild oats | 0 | 0 | 0 | 0 |
| POSTEMERGENCE | | | | |
| Barnyardgrass | 2 | 2 | 1 | 2 |
| Cocklebur | 2 | 1 | 0 | 1 |
| Crabgrass | 1 | 1 | 1 | 1 |
| Downy brome | 1 | 1 | 0 | 1 |
| Giant foxtail | 1 | 1 | 0 | 2 |
| Morningglory | 0 | 0 | 1 | 0 |
| Sorghum | 3 | 2 | 1 | 2 |
| Velvetleaf | 3 | 2 | 1 | 2 |
| Wild oats | 1 | 1 | 0 | 2 |

TEST C

The compounds evaluated in this test were formulated in a non-phytoxic solvent and applied to the soil surface before plant seedlings emerged (preemergence application), to water that covered the soil surface (flood application), and to plants that were in the one-to-four leaf stage (postemergence application). A sandy loam soil was used for the preemergence and postemergence tests, while a silt loam soil was used in the flood test. Water depth was approximately 2.5 cm for the flood test and was maintained at this level for the duration of the test.

Plant species in the preemergence and postemergence tests consisted of barnyardgrass (*Echinochloa crus-galli*), barley (*Hordeum vulgare*), bedstraw (*Galium aparine*), blackgrass (*Alopecurus myosuroides*), chickweed (*Stellaria media*), cocklebur (*Xanthium pensylvanicum*), corn (*Zea mays*), cotton (*Gossypium hirsutum*), crabgrass (*Digitaria sanguinalis*), downy brome (*Bromus tectorum*), giant foxtail (*Setaria faberii*), johnsongrass (*Sorghum halpense*), lambsquarters (*Chenopodium album*), morningglory (*Ipomoea hederacea*), pigweed (*Amaranthus retroflexus*), rape (*Brassica napus*), ryegrass (*Lolium multiflorum*), sorghum (*Sorghum bicolor*), soybean (*Glycine max*), speedwell (*Veronica persica*), sugar beet (*Beta vulgaris*), velvetleaf (*Abutilon theophrasti*), wheat (*Triticum aestivum*), wild buckwheat (*Polygonum convolvulus*), and wild oat (*Avena fatua*). All plant species were planted one day before application of the compound for the preemergence portion of this test. Plantings of these species were adjusted to produce plants of appropriate size for the postemergence portion of the test. Plant species in the flood test consisted of rice (*Oryza sativa*), umbrella sedge (*Cyperus difformis*), duck salad (*Heteranthera limosa*), barnyardgrass (*Echinochloa crus-galli*) and Late watergrass (*Echinocloa oryzicola*) grown to the 1 and 2 leaf stage for testing.

All plant species were grown using normal greenhouse practices. Visual evaluations of injury expressed on treated plants, when compared to untreated controls, were recorded approximately fourteen to twenty one days after application of the test compound. Plant response ratings, summarized in Table C, were recorded on a 0 to 100 scale where 0 is no effect and 100 is complete control. A dash (-) response means no test result.

TABLE C

| Rate 125 g/ha | COMPOUND | | | |
|---|---|---|---|---|
| | 11 | 12 | 14 | 20 |
| POSTEMERGENCE | | | | |
| Barley Igri | 65 | 35 | 45 | 85 |
| Barnyardgrass | 100 | 95 | 85 | 80 |
| Blackgrass | 100 | 40 | 50 | 45 |
| Chickweed | 85 | 45 | 30 | 35 |
| Cocklebur | 55 | 65 | 65 | 70 |
| Corn | 50 | 65 | 35 | 50 |
| Cotton | 100 | 100 | 100 | 100 |
| Crabgrass | 35 | 65 | 80 | 90 |
| Downy Brome | 90 | 55 | 45 | 90 |
| Duck salad | 35 | 20 | 50 | 90 |
| Galium | 100 | 60 | 65 | 70 |
| Giant foxtail | 95 | 95 | 80 | 95 |
| Italn. Rygrass | 100 | 55 | 75 | 100 |
| Johnsongrass | 100 | 95 | 100 | 100 |
| Lambsquarters | 100 | 100 | 100 | 95 |
| Morningglory | 100 | 100 | 100 | 95 |
| Rape | 100 | 100 | 100 | 100 |
| Redroot Pigweed | 100 | 90 | 100 | 100 |
| Rice Japonica | 95 | 80 | 95 | 90 |
| Soybean | 85 | 75 | 90 | 90 |
| Speedwell | 100 | 100 | 100 | — |
| Sugar beet | 100 | 100 | 100 | 100 |
| Umbrella sedge | 100 | 60 | 45 | 90 |
| Velvetleaf | 100 | 100 | 100 | 100 |
| Watergrass 2 | 100 | 100 | 90 | 95 |
| Wheat | 100 | 35 | 45 | 100 |
| Wild buckwheat | 100 | 100 | 100 | 100 |
| Wild oat | 100 | 60 | 65 | 95 |
| 2 Leaf BYG | 100 | 100 | 100 | 95 |
| PREEMERGENCE | | | | |
| Barley Igri | 70 | 15 | 25 | 55 |
| Barnyardgrass | 95 | 100 | 100 | 100 |
| Blackgrass | 100 | 80 | 60 | 95 |
| Chickweed | 100 | 0 | 25 | 60 |
| Cocklebur | 35 | 0 | 85 | 65 |
| Corn | 65 | 0 | 85 | 70 |
| Cotton | 95 | 0 | 90 | 85 |
| Crabgrass | 100 | 95 | 100 | 100 |
| Downy Brome | 90 | 01 | 30 | 55 |
| Galium | 100 | 80 | 90 | 30 |
| Giant foxtail | 100 | 100 | 100 | 100 |
| Italn. Rygrass | 100 | 90 | 80 | 100 |
| Johnsongrass | 100 | 95 | 100 | 100 |
| Lambsquarters | 100 | 100 | 100 | 100 |
| Morningglory | 85 | 30 | 65 | 95 |
| Rape | 100 | 95 | 95 | 100 |
| Redroot Pigweed | 100 | 100 | 90 | 100 |
| Soybean | 60 | 25 | 40 | 90 |
| Speedwell | 100 | 55 | 100 | 100 |
| Sugar beet | 100 | 100 | 100 | 100 |
| Velvetleaf | 100 | 100 | 100 | 100 |
| Wheat | 80 | 45 | 35 | 95 |
| Wild buckwheat | 100 | 100 | 100 | 100 |
| Wild oat | 100 | 55 | 60 | 70 |

TABLE C-continued

| Rate 62 g/ha | COMPOUND | | | | |
|---|---|---|---|---|---|
| | 11 | 12 | 14 | 20 | 22 |
| POSTEMERGENCE | | | | | |
| Barley Igri | 65 | 35 | 45 | 85 | 0 |
| Barnyardgrass | 100 | 65 | 45 | 80 | 95 |
| Blackgrass | 95 | 40 | 50 | 35 | 65 |
| Chickweed | 80 | 30 | 30 | 20 | 95 |
| Cocklebur | 50 | 45 | 45 | 45 | 95 |
| Corn | 35 | 30 | 35 | 50 | 60 |
| Cotton | 100 | 100 | 100 | 100 | 100 |
| Crabgrass | 35 | 35 | 25 | 70 | 35 |
| Downy Brome | 85 | 50 | 45 | 40 | 65 |
| Duck salad | 30 | 0 | 0 | 85 | 60 |
| Galium | 100 | 55 | 65 | 20 | 100 |
| Giant foxtail | 95 | 90 | 45 | 95 | 100 |
| Italn. Rygrass | 95 | 50 | 60 | 90 | 75 |
| Johnsongrass | 90 | 95 | 90 | 100 | 100 |
| Lambsquarters | 100 | 100 | 100 | 95 | 100 |
| Morningglory | 100 | 95 | 100 | 95 | 95 |
| Rape | 100 | 100 | 95 | 80 | 100 |
| Redroot Pigweed | 100 | 90 | 100 | 100 | 100 |
| Rice Japonica | 95 | 70 | 80 | 80 | 75 |
| Soybean | 80 | 75 | 80 | 85 | 75 |
| Speedwell | 100 | 95 | 100 | — | 100 |
| Sugar beet | 100 | 100 | 100 | 100 | 100 |
| Umbrella sedge | 95 | 30 | 30 | 90 | 80 |

TABLE C-continued

| | | | | | |
|---|---|---|---|---|---|
| Velvetleaf | 100 | 90 | 100 | 100 | 100 |
| Watergrass 2 | 100 | 100 | 75 | 95 | 95 |
| Wheat | 95 | 30 | 45 | 95 | 65 |
| Wild buckwheat | 100 | 95 | 100 | 95 | 100 |
| Wild oat | 95 | 60 | 30 | 85 | 85 |
| 2 Leaf BYG | 100 | 100 | 85 | 90 | 95 |

PREEMERGENCE

| | | | | | |
|---|---|---|---|---|---|
| Barley Igri | 50 | 0 | 0 | 35 | 25 |
| Barnyardgrass | 95 | 85 | 80 | 90 | 95 |
| Blackgrass | 100 | 45 | 30 | 80 | 65 |
| Chickweed | 40 | 0 | 0 | 30 | 95 |
| Cocklebur | 10 | 0 | 30 | 50 | 30 |
| Corn | 50 | 0 | 65 | 50 | 65 |
| Cotton | 55 | 0 | 60 | 75 | 0 |
| Crabgrass | 100 | 85 | 90 | 100 | 100 |
| Downy Brome | 70 | 0 | 30 | 55 | 35 |
| Galium | 80 | 40 | 10 | 10 | 100 |
| Giant foxtail | 100 | 95 | 50 | 100 | 90 |
| Italn. Rygrass | 95 | 65 | 40 | 95 | 90 |
| Johnsongrass | 100 | 95 | 100 | 95 | 95 |
| Lambsquarters | 100 | 90 | 100 | 100 | 100 |
| Morningglory | 40 | 0 | 30 | 0 | 80 |
| Rape | 100 | 24 | 0 | 80 | 80 |
| Redroot Pigweed | 100 | 100 | 75 | 100 | 100 |
| Soybean | — | 25 | 35 | 70 | 95 |
| Speedwell | 100 | 40 | 95 | 100 | 100 |
| Sugar beet | 100 | 0 | 100 | 100 | 95 |
| Velvetleaf | 100 | 100 | 100 | 100 | 100 |
| Wheat | 65 | 0 | 0 | 90 | 40 |
| Wild buckwheat | 100 | 45 | 95 | 95 | 100 |
| Wild oat | 85 | 10 | 0 | 70 | 70 |

COMPOUND

| Rate 31 g/ha | 11 | 12 | 14 | 20 | 22 |
|---|---|---|---|---|---|

POSTEMERGENCE

| | | | | | |
|---|---|---|---|---|---|
| Barley Igri | 55 | 35 | 40 | 50 | 0 |
| Barnyardgrass | 85 | 25 | 40 | 80 | 65 |
| Blackgrass | 50 | 35 | 35 | 25 | 60 |
| Chickweed | 65.230 | 30 | 20 | 80 | |
| Cocklebur | 0 | 40 | 40 | 45 | 50 |
| Corn | 0 | 30 | 25 | 50 | 35 |
| Cotton | 100 | 100 | 100 | 100 | 100 |
| Crabgrass | 0 | 30 | 25 | 65 | 10 |
| Downy Brome | 75 | 40 | 35 | 40 | 35 |
| Duck salad | 0 | 0 | 0 | 0 | 10 |
| Galium | 95 | 45 | 45 | 15 | 100 |
| Giant foxtail | 65 | 70 | 45 | 95 | 55 |
| Italn. Rygrass | 85 | 45 | 45 | 80 | 55 |
| Johnsongrass | 60 | 90 | 90 | 95 | 95 |
| Lambsquarters | 100 | 95 | 100 | 95 | 100 |
| Morningglory | 90 | 95 | 90 | 90 | 85 |
| Rape | 95 | 100 | 95 | 65 | 100 |
| Redroot Pigweed | 100 | 65 | 100 | 100 | 100 |
| Rice Japonica | 85 | 65 | 55 | 35 | 70 |
| Soybean | 60 | 75 | 50 | 75 | 75 |
| Speedwell | 100 | 85 | 100 | — | 100 |
| Sugar beet | 100 | 100 | 100 | 85 | 100 |
| Umbrella sedge | 75 | 20 | 0 | 75 | 80 |
| Velvetleaf | 100 | 90 | 100 | 100 | 100 |
| Watergrass 2 | 100 | 85 | 65 | 50 | 80 |
| Wheat | 60 | 25 | 45 | 90 | 45 |
| Wild buckwheat | 100 | 90 | 100 | 80 | 100 |
| Wild oat | 40 | 35 | 20 | 80 | 30 |
| 2 Leaf BYG | 100 | 60 | 50 | 30 | 80 |

PREEMERGENCE

| | | | | | |
|---|---|---|---|---|---|
| Barley Igri | 35 | 0 | 0 | 0 | 0 |
| Barnyardgrass | 85 | 75 | 75 | 65 | 85 |
| Blackgrass | 95 | 20 | 0 | 45 | 50 |
| Chickweed | 40 | 0 | 0 | 0 | 65 |
| Cocklebur | 0 | 0 | 10 | 25 | 20 |
| Corn | 35 | 0 | 20 | 35 | 60 |
| Cotton | 25 | 0 | 0 | 35 | 0 |
| Crabgrass | 90 | 55 | 40 | 100 | 95 |
| Downy Brome | 60 | 0 | 30 | 10 | 0 |
| Galium | 35 | 0 | 0 | 0 | 50 |
| Giant foxtail | 100 | 85 | 15 | 100 | 70 |
| Italn. Rygrass | 95 | 20 | 20 | 45 | 80 |
| Johnsongrass | 100 | 55 | 95 | 95 | 85 |
| Lambsquarters | 100 | 90 | 90 | 100 | 100 |
| Morningglory | 40 | 0 | 0 | 0 | 65 |
| Rape | 100 | 0 | 0 | 45 | 35 |
| Redroot Pigweed | 100 | 100 | 75 | 100 | 100 |
| Soybean | 60 | 10 | 30 | 25 | 65 |
| Speedwell | 100 | 0 | 30 | 100 | 100 |
| Sugar beet | 90 | 0 | 45 | 100 | 80 |
| Velvetleaf | 100 | 100 | 100 | 100 | 100 |
| Wheat | 50 | 0 | 0 | 0 | 0 |
| Wild buckwheat | 95 | 0 | 35 | 90 | 75 |
| Wild oat | 75 | 0 | 0 | 35 | 30 |

COMPOUND

| Rate 16 g/ha | 11 | 12 | 14 | 20 | 22 |
|---|---|---|---|---|---|

POSTEMERGENCE

| | | | | | |
|---|---|---|---|---|---|
| Barley Igri | 45 | 25 | 35 | 50 | 0 |
| Barnyardgrass | 70 | 0 | 35 | 0 | 40 |
| Blackgrass | 35 | 30 | 25 | 25 | 50 |
| Chickweed | 45 | 20 | 20 | 20 | 80 |
| Cocklebur | 0 | 40 | 35 | — | 50 |
| Corn | 0 | 25 | 20 | 35 | 10 |
| Cotton | 65 | 100 | 80 | 100 | 95 |
| Crabgrass | 0 | 30 | 25 | 45 | 10 |
| Downy Brome | 60 | 40 | 30 | 25 | 30 |
| Duck salad | 0 | 0 | 0 | 0 | 0 |
| Galium | — | 45 | 45 | 0 | 0 |
| Giant foxtail | 20 | 20 | 40 | 50 | 45 |
| Italn. Rygrass | 80 | 30 | 45 | 40 | 25 |
| Johnsongrass | 20 | 70 | 85 | 50 | 90 |
| Lambsquarters | 100 | 90 | 95 | 95 | 100 |
| Morningglory | 80 | 65 | 90 | 85 | 85 |
| Rape | 80 | 100 | 85 | 50 | 100 |
| Redroot Pigweed | 85 | 50 | 85 | — | 20 |
| Rice Japonica | 70 | 55 | 35 | 35 | 20 |
| Soybean | 55 | 75 | 45 | 55 | 75 |
| Speedwell | 100 | 85 | 100 | — | 100 |
| Sugar beet | 100 | 100 | 100 | 40 | 100 |
| Umbrella sedge | 70 | 0 | 0 | 65 | 70 |
| Velvetleaf | 90 | 85 | 100 | 100 | 100 |
| Watergrass 2 | 70 | 30 | 0 | 35 | 65 |
| Wheat | 55 | 25 | 35 | 50 | 30 |
| Wild buckwheat | 95 | 90 | 70 | 35 | 100 |
| Wild oat | 30 | 30 | 10 | 65 | 25 |
| 2 Leaf BYG | 80 | 40 | 25 | 20 | 60 |

PREEMERGENCE

| | | | | | |
|---|---|---|---|---|---|
| Barley Igri | 35 | 0 | 0 | 0 | 0 |
| Barnyardgrass | 65 | 0 | 0 | 65 | 30 |
| Blackgrass | 95 | 0 | 0 | 25 | 40 |
| Chickweed | 0 | 0 | 0 | 0 | 40 |
| Cocklebur | 0 | 0 | 0 | 0 | 0 |
| Corn | 20 | 0 | 0 | 0 | 0 |
| Cotton | 25 | 0 | 0 | 10 | 0 |
| Crabgrass | 85 | 50 | 40 | 60 | 95 |
| Downy Brome | 50 | 0 | 30 | 10 | 0 |
| Galium | 0 | 0 | 0 | 0 | 0 |
| Giant foxtail | 95 | 0 | 10 | 50 | 70 |
| Italn. Rygrass | 85 | 0 | 0 | 35 | 10 |
| Johnsongrass | 95 | 30 | 35 | 90 | 75 |
| Lambsquarters | 100 | 70 | 80 | 100 | 100 |
| Morningglory | 35 | 0 | 0 | 0 | 65 |
| Rape | 100 | 0 | 0 | 25 | 0 |
| Redroot Pigweed | 100 | 70 | 45 | 100 | 100 |
| Soybean | 30 | 0 | 0 | 10 | 40 |
| Speedwell | 100 | 0 | 0 | 0 | 90 |
| Sugar beet | — | 0 | 0 | 95 | 80 |
| Velvetleaf | 100 | 40 | 100 | 0 | 100 |
| Wheat | 30 | 0 | 0 | 0 | 0 |
| Wild buckwheat | 75 | 0 | 30 | 80 | 60 |
| Wild oat | 40 | 0 | 0 | 35 | 15 |

TABLE C-continued

| | COMPOUND |
|---|---|
| Rate 8 g/ha | 22 |
| POSTEMERGENCE | |
| Barley Igri | 0 |
| Barnyardgrass | 35 |
| Blackgrass | 35 |
| Chickweed | 70 |
| Cocklebur | 35 |
| Corn | 10 |
| Cotton | 95 |
| Crabgrass | 0 |
| Downy Brome | 30 |
| Duck salad | 0 |
| Galium | 0 |
| Giant foxtail | 30 |
| Italn. Rygrass | 0 |
| Johnsongrass | 75 |
| Lambsquarters | 95 |
| Morningglory | 85 |
| Rape | 85 |
| Redroot Pigweed | 10 |
| Rice Japonica | 5 |
| Soybean | 65 |
| Speedwell | 40 |
| Sugar beet | 80 |
| Umbrella sedge | 10 |
| Velvetleaf | 100 |
| Watergrass 2 | 20 |
| Wheat | 30 |
| Wild buckwheat | 75 |
| Wild oat | 20 |
| 2 Leaf BYG | 10 |
| PREEMERGENCE | |
| Barley Igri | 0 |
| Barnyardgrass | 10 |
| Blackgrass | 0 |
| Chickweed | 0 |
| Cocklebur | 0 |
| Corn | 0 |
| Cotton | 0 |
| Crabgrass | 95 |
| Downy Brome | 0 |
| Galium | 0 |
| Giant foxtail | 55 |
| Italn. Rygrass | 0 |
| Johnsongrass | 50 |
| Lambsquarters | 95 |
| Morningglory | 60 |
| Rape | 0 |
| Redroot Pigweed | 90 |
| Soybean | 10 |
| Speedwell | 0 |
| Sugar beet | 35 |
| Velvetleaf | 65 |
| Wheat | 0 |
| Wild buckwheat | 45 |
| Wild oat | 0 |

TEST D

Seeds of barnyardgrass (*Echinochloa crus-galli*), bindweed (*Convolvolus erubescens*), black nightshade (*Solanum ptycanthum dunal*), cassia (*Cassia unifloria*), cocklebur (*Xanthium pensylvanicum*), common ragweed (*Ambrosia artemisiifolia*), corn (*Zea mays*), cotton (*Gossypium hirsutam*), crabgrass (*Digitaria spp.*), fall panicum (*Panicum dichotomifiorum*), giant foxtail (*Setaria faberii*), green foxtail (*Setaria viridis*), jimsonweed (*Datura stramonium*), johnson grass (*Sorghum halepense*), lambsquarter (*Chenpopdium album*), morningglory (*Ipomoea spp.*), pigweed (*Amaranthus retroflexus*), prickly sida (*Sida spinosa*), shattercane (*Sorghum vulgare*), signalgrass (*Brachiaria platyphylla*), smartweed (*Polygonum persicaria*), soybean (*Glycine max*), sunflower (*Helianthus annuus*), velvetleaf (*Abutilon theophrasti*), wild proso (*Pancium miliaceum*), wooly cup grass (*Eriochloa villosa*), yellow foxtail (*Setaria lutescens*) and purple nutsedge (*Cyperus rotundus*) tubers were planted into a matapeake sandy loam soil. These crops and weeds were grown in the greenhouse until the plants ranged in height from two to eighteen cm (one to four leaf stage), then treated postemergence with the test chemicals dissolved in a non-phytotoxic solvent. Pots receiving these postemergence treatments were placed in the greenhouse and maintained according to routine greenhouse procedures. Treated plants and untreated controls were maintained in the greenhouse approximately 14–21 days after application of the test compound. Visual evaluations of plant injury responses were then recorded. Plant response ratings, summarized in Table D, are reported on a 0 to 100 scale where 0 is no effect and 100 is complete control.

TABLE D

| PREEMERGENCE | |
|---|---|
| | COMPOUND |
| Rate 280 g/ha | 12 |
| Barnyardgrass | 100 |
| Bindweed | 100 |
| Blk Nightshade | 100 |
| Cassia | 70 |
| Cocklebur | 55 |
| Corn | 80 |
| Cotton | 90 |
| Crabgrass | 100 |
| Fall Panicum | 100 |
| Giant Foxtail | 100 |
| Green Foxtail | 100 |
| Jimson Weed | 100 |
| Johnson Grass | 100 |
| Lambsquarter | 100 |
| Morningglory | 100 |
| Nustedge | 25 |
| Pigweed | 100 |
| Prickly Sida | 100 |
| Ragweed | 90 |
| Shattercane | 95 |
| Signalgrass | 100 |
| Smartweed | 100 |
| Soybean | 100 |
| Sunflower | 80 |
| Velvetleaf | 100 |
| Wild Proso | 100 |
| Wolly Cup Grass | 95 |
| Yellow Foxtail | 100 |
| | COMPOUND |
| Rate 17.5 g/ha | 12 |
| Barnyardgrass | 65 |
| Bindweed | 0 |
| Blk Nightshade | 0 |
| Cassia | 100 |
| Cocklebur | 0 |
| Corn | 0 |
| Cotton | 0 |
| Crabgrass | 60 |
| Fall Panicum | 65 |
| Giant Foxtail | 60 |
| Green Foxtail | 55 |
| Jimson Weed | 15 |
| Johnson Grass | 80 |
| Lambsquarter | 100 |
| Morningglory | 0 |
| Nustedge | 0 |
| Pigweed | 65 |
| Prickly Sida | 50 |
| Ragweed | 15 |

TABLE D-continued

| | |
|---|---|
| Shattercane | 15 |
| Signalgrass | 20 |
| Smartweed | 70 |
| Soybean | 0 |
| Sunflower | 0 |
| Velvetleaf | 50 |
| Wild Proso | 20 |
| Wolly Cup Grass | 10 |
| Yellow Foxtail | 55 |

| | COMPOUND |
|---|---|
| Rate 140 g/ha | 12 |
| Barnyardgrass | 100 |
| Bindweed | 100 |
| Blk Nightshade | 100 |
| Cassia | 50 |
| Cocklebur | 25 |
| Corn | 70 |
| Cotton | 65 |
| Crabgrass | 100 |
| Fall Panicum | 100 |
| Giant Foxtail | 100 |
| Green Foxtail | 100 |
| Jimson Weed | 100 |
| Johnson Grass | 100 |
| Lambsquarter | 100 |
| Morningglory | 45 |
| Nustedge | 15 |
| Pigweed | 100 |
| Prickly Sida | 100 |
| Ragweed | 90 |
| Shattercane | 80 |
| Signalgrass | 90 |
| Smartweed | 100 |
| Soybean | 65 |
| Sunflower | 65 |
| Velvetleaf | 100 |
| Wild Proso | 100 |
| Wolly Cup Grass | 80 |
| Yellow Foxtail | 90 |

| | COMPOUND |
|---|---|
| Rate 70 g/ha | 12 |
| Barnyardgrass | 95 |
| Bindweed | 100 |
| Blk Nightshade | 100 |
| Cassia | 30 |
| Cocklebur | 15 |
| Corn | 55 |
| Cotton | 15 |
| Crabgrass | 100 |
| Fall Panicum | 100 |
| Giant Foxtail | 100 |
| Green Foxtail | 100 |
| Jimson Weed | 70 |
| Johnson Grass | 100 |
| Lambsquarter | 100 |
| Morningglory | 30 |
| Nustedge | 0 |
| Pigweed | 100 |
| Prickly Sida | 100 |
| Ragweed | 50 |
| Shattercane | 60 |
| Signalgrass | 90 |
| Smartweed | 100 |
| Soybean | 15 |
| Sunflower | 25 |
| Velvetleaf | 100 |
| Wild Proso | 80 |
| Wolly Cup Grass | 65 |
| Yellow Foxtail | 85 |

| | COMPOUND |
|---|---|
| Rate 35 g/ha | 12 |
| Barnyardgrass | 75 |
| Bindweed | 15 |

TABLE D-continued

| | |
|---|---|
| Blk Nightshade | 100 |
| Cassia | 0 |
| Cocklebur | 0 |
| Corn | 25 |
| Cotton | 0 |
| Crabgrass | 65 |
| Fall Panicum | 100 |
| Giant Foxtail | 75 |
| Green Foxtail | 75 |
| Jimson Weed | 55 |
| Johnson Grass | 85 |
| Lambsquarter | 100 |
| Morningglory | 0 |
| Nustedge | 0 |
| Pigweed | 80 |
| Prickly Sida | 65 |
| Ragweed | 50 |
| Shattercane | 15 |
| Signalgrass | 60 |
| Smartweed | 95 |
| Soybean | 0 |
| Sunflower | 15 |
| Velvetleaf | 70 |
| Wild Proso | 40 |
| Wolly Cup Grass | 10 |
| Yellow Foxtail | 65 |

TEST E

Seeds, rhizomes, or plant parts of alfalfa (*Medicago sativa*), annual bluegrass (*Poa annua*), bermudagrass (*Cynodon dactylon*), broadleaf signalgrass (*Brachiaria platyphylia*), common purslane (*Portulaca oleracea*), common ragweed (*Ambrosia artemisiifolia*), dallisgrass (*Paspalum dilatatum*), goosegrass (*Eleusine indica*), guineagrass (*Panicum maximum*), itchgrass (*Rottboellia cochinchinensis*), johnsongrass (*Sorghum halepense*), large crabgrass (*Digitaria sanguinalis*), peanut (*Arachis hypoagaea*), pitted morningglory (*Ipomoea lacunosa*), purple nutsedge (*Cyperus rotundus*), sandbur (*Southern sandbur*), smooth crabgrass (*Digitaria ischaemum*) were planted into greenhouse pots containing greenhouse planting medium. Each pot contained only one plant species.

The test compound was dissolved in a non-phytotoxic solvent and applied preemergence and/or postemergence to the plants. Preemergence applications were made within one day of planting the seeds or plant parts. Postemergence applications were applied when the plants were in the two to four leaf stage (three to twenty cm). Untreated control plants and treated plants were placed in the greenhouse and visually evaluated for injury at 14 to 28 days after herbicide application. Plant response ratings, summarized in Table E, are based on a 0 to 100 scale where 0 is no injury and 100 is complete control. A dash (-) response indicates no test result.

TABLE 3

| | COMPOUND |
|---|---|
| Rate 0500 g/ha | 11 |
| POSTEMERGENCE | |
| Alfalfa Var. | 100 |
| Ann Bluegrass | 100 |
| Bermudagrass | 100 |
| Brdlf Sgnlgrass | 100 |
| Cmn Purslane | 100 |
| Cmn Ragweed | 100 |
| Dallisgrass | 100 |
| Goosegrass | 100 |

TABLE 3-continued

| | |
|---|---|
| Guineagrass | 100 |
| Itchgrass | 100 |
| Johnsongrass | 98 |
| Large Crabgrass | 95 |
| Peanuts | 95 |
| Pit Morninglory | 70 |
| Purple Nustedge | 75 |
| S. Sandbur | 100 |
| Smooth Crabgras | 90 |
| PREEMERGENCE | |
| Alfalfa Var. | 100 |
| Ann Bluegrass | 100 |
| Bermudagrass | 100 |
| Brdlf Sgnlgrass | 100 |
| Cmn Purslane | 100 |
| Cmn Ragweed | 100 |
| Dallisgrass | 100 |
| Goosegrass | 100 |
| Guineagrass | 100 |
| Itchgrass | 98 |
| Johnsongrass | 100 |
| Large Crabgrass | 100 |
| Peanuts | 60 |
| Pit Morninglory | 10 |
| Purple Nustedge | 90 |
| S. Sandbur | 100 |
| Smooth Crabgras | 100 |

| | COMPOUND | | |
|---|---|---|---|
| Rate 0250 g/ha | 1 | 8 | 11 |
| Alfalfa Var. | 0 | 20 | 98 |
| Ann Bluegrass | 0 | 50 | 95 |
| Bermudagrass | 0 | 40 | 98 |
| Brdlf Sgnlgrass | 0 | 70 | 100 |
| Cmn Purslane | 30 | 50 | 100 |
| Cmn Ragweed | — | — | 100 |
| Dallisgrass | 0 | 0 | 100 |
| Goosegrass | 20 | 40 | 90 |
| Guineagrass | 0 | 90 | 75 |
| Itchgrass | 0 | 60 | 95 |
| Johnsongrass | 0 | 70 | 100 |
| Large Crabgrass | 0 | 50 | 80 |
| Peanuts | 0 | 60 | 98 |
| Pit Morninglory | 0 | 70 | 75 |
| Purple Nustedge | 0 | 40 | 80 |
| S. Sandbur | — | 50 | 95 |
| Smooth Crabgras | 0 | 70 | 75 |
| PREEMERGENCE | | | |
| Alfalfa Var. | 30 | 100 | 100 |
| Ann Bluegrass | 0 | 80 | 100 |
| Bermudagrass | 20 | 100 | 100 |
| Brdlf Sgnlgrass | 0 | 100 | 100 |
| Cmn Purslane | 0 | 100 | 100 |
| Cmn Ragweed | — | — | 100 |
| Dallisgrass | 40 | 100 | 100 |
| Goosegrass | 50 | 100 | 100 |
| Guineagrass | 80 | 100 | 100 |
| Itchgrass | 0 | 90 | 100 |
| Johnsongrass | 0 | 100 | 100 |
| Large Crabgrass | 60 | 100 | 100 |
| Peanuts | 0 | 20 | 60 |
| Pit Morninglory | 0 | 0 | 100 |
| Purple Nustedge | 0 | 0 | 80 |
| S. Sandbur | 50 | 100 | 100 |
| Smooth Crabgras | 30 | 100 | 100 |

| | COMPOUND | | |
|---|---|---|---|
| Rate 0125 g/ha | 8 | 11 | 34 |
| POSTEMERGENCE | | | |
| Alfalfa Var. | 0 | 50 | 20 |
| Ann Bluegrass | 0 | 65 | 20 |
| Bermudagrass | 0 | 98 | 60 |
| Brdlf Sgnlgrass | 50 | 20 | 10 |
| Cmn Purslane | 50 | 80 | 10 |
| Cmn Ragweed | — | 95 | — |
| Dallisgrass | 0 | 65 | 0 |
| Goosegrass | 20 | 50 | 10 |
| Guineagrass | 70 | 20 | 0 |
| Itchgrass | 60 | 40 | 0 |
| Johnsongrass | 20 | 40 | 10 |
| Large Crabgrass | 0 | 30 | 0 |
| Peanuts | 30 | 60 | 30 |
| Pit Morninglory | 30 | 20 | 90 |
| Purple Nustedge | — | 20 | 60 |
| S. Sandbur | 30 | 30 | 0 |
| Smooth Crabgras | 30 | 15 | 0 |
| PREEMERGENCE | | | |
| Alfalfa Var. | 30 | 100 | 60 |
| Ann Bluegrass | 80 | 90 | 0 |
| Bermudagrass | 100 | 90 | 100 |
| Brdlf Sgnlgrass | 80 | 100 | 40 |
| Cmn Purslane | 100 | 100 | 100 |
| Cmn Ragweed | — | 100 | — |
| Dallisgrass | 100 | 100 | 80 |
| Goosegrass | 100 | 100 | 100 |
| Guineagrass | 100 | 100 | 100 |
| Itchgrass | 90 | 80 | 20 |
| Johnsongrass | 100 | 100 | 30 |
| Large Crabgrass | 100 | 100 | 80 |
| Peanuts | 20 | 10 | 0 |
| Pit Morninglory | 0 | 10 | 50 |
| Purple Nustedge | 0 | 20 | 0 |
| S. Sandbur | 100 | 90 | 60 |
| Smooth Crabgras | 100 | 90 | 80 |

What is claimed is:

1. A compound of Formula I:

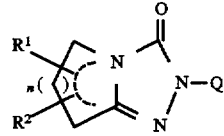

wherein the left-hand ring contains only single bonds or one bond in the ring is a double bond;

n is 2;

$R^1$ is selected from the group H, halogen; hydroxy, $C_1$–$C_3$ alkoxy; $C_1$–$C_3$ haloalkoxy; $C_2$–$C_5$ alkylcarbonyloxy; or $C_2$–$C_5$ haloalkylcarbonyloxy;

$R^2$ is selected from the group H, hydroxy, and halogen; or when $R^1$ and $R^2$ are bonded to the same carbon atom they can be taken together along with the carbon to which they are attached to form C=O; or when $R^1$ and $R^2$ are bonded to adjacent carbon atoms they can be taken together along with the carbons to which they are attached to form

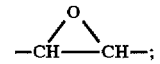

51

Q is selected from the group

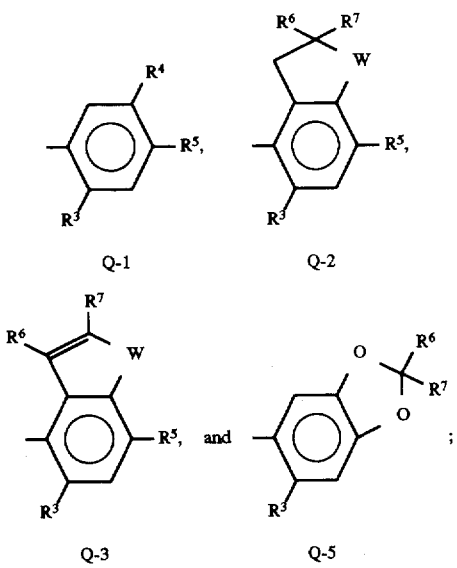

Q-1    Q-2

Q-3    Q-5

$R^3$ is selected from the group H and halogen;

$R^4$ is selected from the group H, $C_1$–$C_8$ alkyl, $C_1$–$C_8$ haloalkyl, halogen, $OR^9$, $S(O)_mR^9$, $COR^9$, $CO_2R^9$, $C(O)SR^9$, $C(O)NR^{11}R^{12}$, CHO, $CR^7$=$CR^7CO_2R^9$, $CO_2N$=$CR^{13}R^{14}$, $NO_2$, CN, $NHSO_2R^{15}$ and $NHSO_2NHR^{15}$;

m is 0, 1 or 2;

$R^5$ is selected from the group $C_1$–$C_2$ alkyl, $C_1$–$C_2$ haloalkyl, $OCH_3$, $SCH_3$, $OCHF_2$, halogen, CN and $NO_2$;

$R^6$ is selected from the group H, $C_1$–$C_3$ alkyl, $C_2$–$C_3$ alkynyl, $C_2$–$C_3$ haloalkynyl, $CO_2(C_1$–$C_4$ alkyl), and halogen;

$R^7$ is independently selected from the group H, $C_1$–$C_3$ alkyl and halogen; or when Q is Q-2 or Q-6, $R^6$ and $R^7$ together with the carbon to which they are attached can be C=O;

$R^9$ is selected from the group $C_1$–$C_8$ alkyl; $C_3$–$C_8$ cycloalkyl; $C_3$–$C_8$ alkenyl; $C_3$–$C_8$ alkynyl; $C_1$–$C_8$ haloalkyl; $C_2$–$C_8$ alkoxyalkyl; $C_2$–$C_8$ alkylthioalkyl; $C_2$–$C_8$ alkylsulfinylalkyl; $C_2$–$C_8$ alkylsulfonylalkyl; $C_1$–$C_8$ alkylsulfonyl; phenylsulfonyl optionally substituted on the phenyl ring with halogen or $C_1$–$C_4$ alkyl; $C_4$–$C_8$ alkoxyalkoxyalkyl, $C_4$–$C_8$ cycloalkylalkyl; $C_4$–$C_8$ alkenoxyalkyl; $C_4$–$C_8$ alkynoxyalkyl; $C_6$–$C_8$ cycloalkoxyalkyl; $C_4$–$C_8$ alkenyloxyalkyl; $C_4$–$C_8$ alkynyloxyalkyl; $C_3$–$C_8$ haloalkoxyalkyl; $C_4$–$C_8$ haloalkenoxyalkyl; $C_4$–$C_8$ haloalkynoxyalkyl; $C_6$–$C_8$ cycloalkylthioalkyl; $C_4$–$C_8$ alkenylthioalkyl; $C_4$–$C_8$ alkynylthioalkyl; $C_1$–$C_4$ alkyl substituted a substituent selected from phenoxy and benzyloxy, each ring optionally substituted with a substituent selected from halogen, $C_1$–$C_3$ alkyl and $C_1$–$C_3$haloalkyl; $C_4$–$C_8$ trialkylsilylalkyl; $C_3$–$C_8$ cyanoalkyl; $C_3$–$C_8$ halocycloalkyl; $C_3$–$C_8$ haloalkenyl; $C_5$–$C_8$ alkoxyalkenyl; $C_5$–$C_8$ haloalkoxyalkenyl; $C_5$–$C_8$ alkylthioalkenyl; $C_3$–$C_8$ haloalkynyl; $C_5$–$C_8$ alkoxyalkynyl; $C_5$–$C_8$ haloalkoxyalkynyl; $C_5$–$C_8$ alkylthioalkynyl; $C_2$–$C_8$ alkyl carbonyl; benzyl optionally substituted with a substituent selected from the group halogen, $C_1$–$C_3$ alkyl and $C_1$–$C_3$ haloalkyl; $CHR^{16}COR^{10}$; $CHR^{16}CO_2R^{10}$; $CHR^{16}P(O)(OR^{10})_2$; $CHR^{16}P(S)(OR^{10})_2$; $CHR^{16}C(O)NR^{11}R^{12}$; and $CHR^{16}C(O)NH_2$;

52

$R^{10}$ is selected from the group $C_1$–$C_6$ alkyl, $C_1$–$C_6$ alkenyl and $C_1$–$C_6$ alkynyl;

$R^{11}$ and $R^{13}$ are independently selected from the group H and $C_1$–$C_4$ alkyl;

$R^{12}$ and $R^{14}$ are independently selected from the group $C_1$–$C_4$ alkyl and phenyl optionally substituted with a substituent selected from the group halogen, $C_1$–$C_3$ alkyl and $C_1$–$C_3$ haloalkyl;

$R^{13}$ and $R^{14}$ may be taken together with the carbon to which they are attached to form $C_3$–$C_8$ cycloalkyl;

$R^{15}$ is selected from the group $C_1$–$C_4$ alkyl and $C_1$–$C_4$ haloalkyl;

$R^{16}$ is selected from the group H and $C_1$–$C_3$ alkyl; and

W is selected from the group O and S;

provided that $R^1$ is other than H when the left-hand ring contains only single bonds.

2. A of claim 1 wherein:

$R^1$ is halogen;

$R^2$ is selected from the group H, and halogen;

Q is selected from the group consisting of Q-1 and Q-2

$R^3$ is halogen;

$R^5$ is selected from the group $C_1$–$C_2$ haloalkyl, $OCH_3$, $OCHF_2$, CN, $NO_2$, and halogen;

$R^6$ is selected from the group H, $C_1$–$C_3$ alkyl, $C_2$–$C_3$ alkynyl, $C_2$–$C_3$ haloalkynyl, and halogen;

$R^7$ is H; and

W is O.

3. A compound of claim 2 wherein:

$R^4$ is selected from the group halogen, $OR^9$, $S(O)_mR^9$, $COR^9$, $CO_2R^9$, $C(O)NR^{11}R_2$, CH=$CHCO_2R^9$, $NHSO_2R^{15}$ and $NHSO_2NHR^{15}$;

$R^5$ is halogen;

$R^6$ is selected from the group H and $C_1$–$C_3$ alkyl;

$R^7$ is H; and $R^9$ is selected from the group $C_1$–$C_8$ alkyl; $C_3$–$C_8$ cycloalkyl; $C_3$–$C_8$ alkenyl; $C_3$–$C_8$ alkynyl; $C_1$–$C_8$ haloalkyl; $C_2$–$C_8$ alkoxyalkyl; $C_1$–$C_4$ alkyl substituted with a substituent selected from phenoxy and benzyloxy, each ring optionally substituted with a substituent selected from halogen, $C_1$–$C_3$ alkyl and $C_{1-3}$ haloalkyl; $C_3$–$C_8$ haloalkenyl; $C_3$–$C_8$ haloalkynyl; $C_2$–$C_8$ alkyl carbonyl; benzyl optionally substituted with a substituent selected from the group halogen, $C_1$–$C_3$ alkyl and $C_1$–$C_3$ haloalkyl; $CHR^{16}COR^{10}$; $CHR^{16}CO_2R^{10}$; $CHR^{16}P(O)(OR^{10})_2$; $CHR^{16}C(O)NR^{11}R^{12}$; and $CHR^{16}C(O)NH_2$.

4. The compound of claim 3 which is:

[2,5,6,7-tetrahydro-2-[2,4-dichloro-5-(2-propynyloxy) phenyl]-6-fluoro-3H-pyrrolo[2,1-c]-1,2,4triazol-3-one; and]

5,6,7,8-tetrahydro-2-8-[2,4-dichloro-5-(2propynyloxy)phenyl]-8chloro-1,2,4-triazolo[4,3-α pyridin-3(2H)-one.

5. An agriculturally suitable composition for controlling the growth of undesired vegetation comprising an effective amount of a compound of claim 1 and at least one of a surfactant, solid or liquid diluent.

6. An agriculturally suitable composition for controlling the growth of undesired vegetation comprising an effective amount of a compound of claim 2 and at least one of a surfactant, solid or liquid diluent.

7. An agriculturally suitable composition for controlling the growth of undesired vegetation comprising an effective amount of a compound of claim 3 and at least one of a surfactant, solid or liquid diluent.

8. An agriculturally suitable composition for controlling the growth of undesired vegetation comprising an effective amount of a compound of claim 4 and at least one of a surfactant, solid or liquid diluent.

9. A method for controlling the growth of undesired vegetation comprising applying to the locus to be protected an effective amount of the composition of claim 5.

10. A method for controlling the growth of undesired vegetation comprising applying to the locus to be protected an effective amount of a composition of claim 8.

* * * * *

UNITED STATES PATENT AND TRADEMARK OFFICE
CERTIFICATE OF CORRECTION

PATENT NO. : 5,728,651
DATED : March 17, 1998
INVENTOR(S) : Hong et al.

It is certified that error appears in the above-identified patent and that said Letters Patent is hereby corrected as shown below:

Column 3, lines 16-17, delete "$C_1$-$C_6$ alkenyl and $C_1$-$C_6$ alkynyl" and substitute therefor "$C_2$-$C_6$ alkenyl and $C_2$-$C_6$ alkynyl".

Column 5, lines 41-42, delete "$C_1$-$C_6$ alkenyl and $C_1$-$C_6$ alkynyl" and substitute therefor "$C_2$-$C_6$ alkenyl and $C_2$-$C_6$ alkynyl".

Column 6, line 28, delete "Preferred compounds of the invention are:" and substitute therefor "Preferred compound of the invention is:".

Column 6, lines 30-32, delete "2,5,6,7-tetrahydro-2-[2,4-dichloro-5-(2-propynyloxy)phenyl]-6-fluoro-3H-pyrrolo[2,1-c]-1,2,4-triazol-3-one; and".

Column 6, line 34, delete "[4,3-α]pyridin-3(2H)" and substitute therefor "[4,3-a]pyridin-3(2*H*).

Column 52, lines 1-2, delete "$C_1$-$C_6$ alkenyl and $C_1$-$C_6$ alkynyl" and substitute therefor "$C_2$-$C_6$ alkenyl and $C_2$-$C_6$ alkynyl".

Column 52, lines 54-56, delete " 2,5,6,7-tetrahydro-2-[2,4-dichloro-5-(2-propynyloxy)phenyl]-6-fluoro-3H-pyrrolo[2,1-c]-1,2,4-triazol-3-one; and]"

UNITED STATES PATENT AND TRADEMARK OFFICE
CERTIFICATE OF CORRECTION

PATENT NO. : 5,728,651
DATED : March 17, 1998
INVENTOR(S) : Hong et al.

It is certified that error appears in the above-identified patent and that said Letters Patent is hereby corrected as shown below:

Column 52, lines 57-59, delete " [ 5,6,7,8-tetrahydro-2-8-[2,4-dichloro-5-(2propynyloxy)phenyl]-8chloro-1,2,4-triazolo[4,3-α pyridin-3(2H)-one" and substitute therefor "5,6,7,8-tetrahydro-2-[2,4-dichloro-5-(2-propynyloxy)pehnyl]-8-chloro-1,2,4-triazolo[4,3-a]pyridin-3(2*H*)-one ].

Signed and Sealed this

Sixth Day of April, 1999

Attest:

Q. TODD DICKINSON

Attesting Officer

Acting Commissioner of Patents and Trademarks